United States Patent
David et al.

(10) Patent No.: US 10,947,275 B2
(45) Date of Patent: *Mar. 16, 2021

(54) CAGED CELL PENETRATING PEPTIDE-POLYMER CONJUGATES FOR DIAGNOSTIC AND THERAPEUTIC APPLICATIONS

(71) Applicant: Ben-Gurion University of the Negev Research and Development Authority, Beer Sheva (IL)

(72) Inventors: Ayelet David, Omer (IL); Gonen Ashkenasy, Omer (IL); Yosi Shamay, Kfar Sabbah (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 82 days.

This patent is subject to a terminal disclaimer.

(21) Appl. No.: 16/205,275

(22) Filed: Nov. 30, 2018

(65) Prior Publication Data

US 2019/0225653 A1 Jul. 25, 2019

Related U.S. Application Data

(63) Continuation of application No. 13/700,847, filed as application No. PCT/IL2011/000413 on May 26, 2011, now Pat. No. 10,167,319.

(60) Provisional application No. 61/349,819, filed on May 29, 2010.

(51) Int. Cl.
| | | |
|---|---|---|
| *A61K 49/14* | (2006.01) | |
| *A61K 51/00* | (2006.01) | |
| *A61K 51/08* | (2006.01) | |
| *A61K 49/00* | (2006.01) | |
| *C07K 9/00* | (2006.01) | |
| *A61K 47/64* | (2017.01) | |
| *A61K 47/32* | (2006.01) | |

(52) U.S. Cl.
CPC .............. *C07K 9/001* (2013.01); *A61K 47/32* (2013.01); *A61K 47/64* (2017.08); *A61K 49/0002* (2013.01); *A61K 49/0056* (2013.01)

(58) Field of Classification Search
CPC .... A61K 47/00; A61K 49/00; A61K 2121/00; A61K 2123/00; A61K 47/64; A61K 47/32; A61K 49/0056; A61K 49/0002; A61K 51/00; A61K 51/08; A61K 51/088; A61K 49/14; C07K 9/001
USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.2, 514/21.3, 2, 21.4, 21.5, 21.6, 21.7; 530/300, 324, 325, 326, 327, 328
See application file for complete search history.

(56) References Cited

U.S. PATENT DOCUMENTS

| | | |
|---|---|---|
| 6,027,709 A | 2/2000 | Little et al. |
| 6,593,148 B1 | 7/2003 | Narayanan |
| 6,995,274 B2 | 2/2006 | Lugade et al. |
| 7,005,518 B2 | 2/2006 | Peng et al. |
| 7,115,707 B2 | 10/2006 | Ben-Sasson et al. |
| 7,459,145 B2 | 12/2008 | Bao et al. |
| 7,504,089 B2 | 3/2009 | Lugade et al. |
| 7,534,431 B2 | 5/2009 | McBride et al. |
| 7,579,318 B2 | 8/2009 | Divita et al. |
| 8,840,874 B2 | 9/2014 | David et al. |
| 10,167,319 B2* | 1/2019 | David ............... A61K 49/0002 |
| 2008/0318246 A1 | 12/2008 | Lawrence et al. |
| 2009/0186802 A1 | 7/2009 | Alluis et al. |
| 2010/0048487 A1 | 2/2010 | Uno et al. |
| 2010/0111949 A1 | 5/2010 | Qin et al. |

FOREIGN PATENT DOCUMENTS

| | | |
|---|---|---|
| EP | 1797901 A1 | 6/2007 |
| WO | WO 2004/045547 A2 | 6/2004 |
| WO | WO 2005/065418 A2 | 7/2005 |
| WO | WO 2007/134236 A2 | 11/2007 |
| WO | WO 2009/012109 A2 | 1/2009 |
| WO | WO 2009/133545 A2 | 11/2009 |
| WO | WO 2010/055929 A1 | 5/2010 |

OTHER PUBLICATIONS

Ammi et al. IEEE Transactions on Ultrasonics, Ferroelectrics, and Frequency Control, 2006, vol. 53, No. 1, p. 126-136.
Carey, British Medical Journal, 1987, vol. 295, p. 907-908.
Dvir T. et al. Nano Lett 2010, vol. 10, p. 250-154.
Huber et al. Bioconjugate Chem., 1998, vol. 9, p. 242-249.
Katayama, et al. Chem Commun (Camb) 2008, vol. 42, p. 5399-401.
Shamay et al. Biomaterials, 2010 (available online), vol. 32, p. 1377-1386.
Takeuchi et al. ACS Chemical Biology, 2006, vol. 1, No. 5, pp. 299-303.
Watai et al., "Regulation of nuclear import by light-induced activation of caged nuclear localization signal in living cells", FEBS Letters, vol. 488, No. 1-2, Jan. 12, 2001, p. 39-44.

* cited by examiner

*Primary Examiner* — D. L. Jones
(74) *Attorney, Agent, or Firm* — Cooley LLP; Ivor R. Elrifi; Matthew Pavao

(57) ABSTRACT

The caged cell-penetrating peptide (cCPP) conjugates of this invention are ideal for intracellular delivery of a broad variety of cargoes including various nanoparticle pharmaceutical carriers (liposomes, micelles, microparticles, nanoparticles, polymer-conjugates). The conjugates comprise a detectable agent or a therapeutic agent, and the conjugates provide a novel strategy for site-specific delivery of the same to appropriate tissues in the subject. Versatile application of the conjugates in diagnostics and imaging is described.

11 Claims, 11 Drawing Sheets
Specification includes a Sequence Listing.

Merge

FITC

20μm

LysoTracker Red

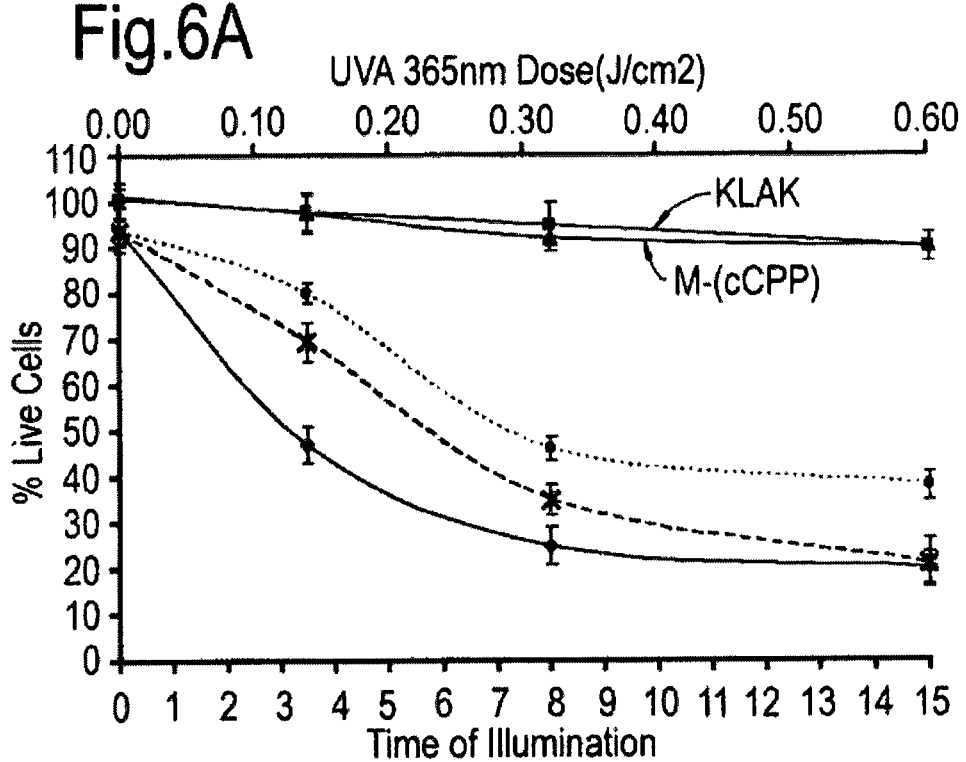
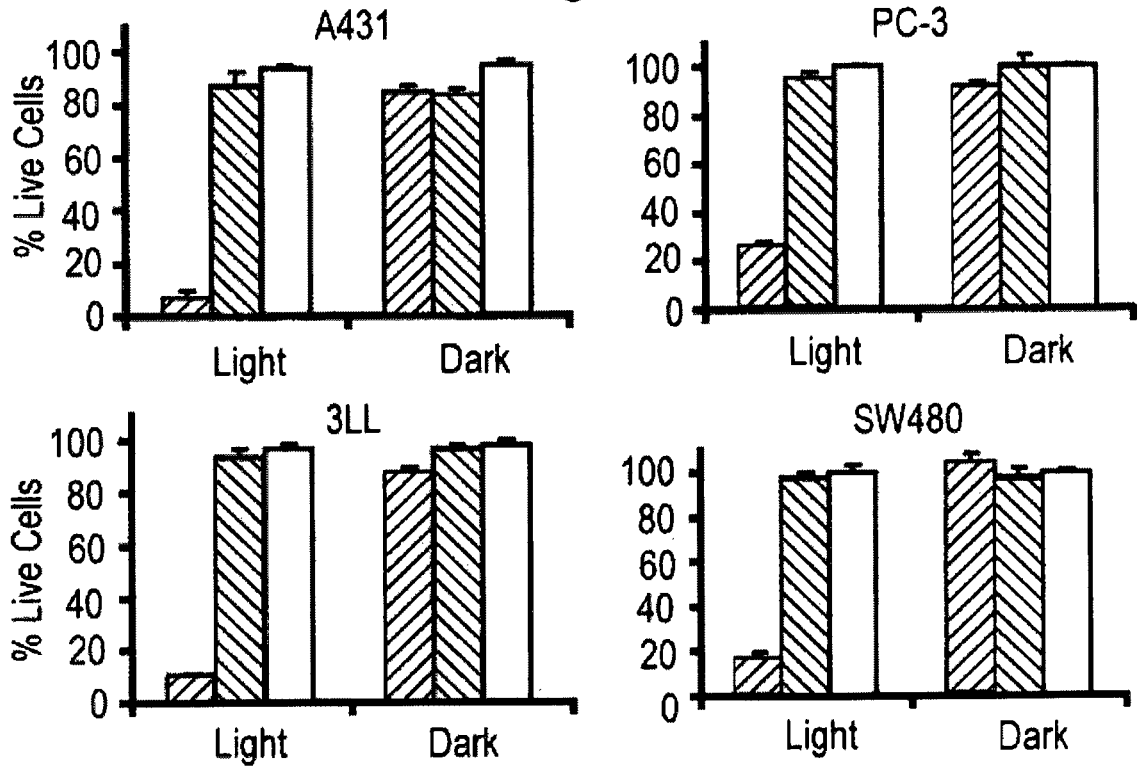

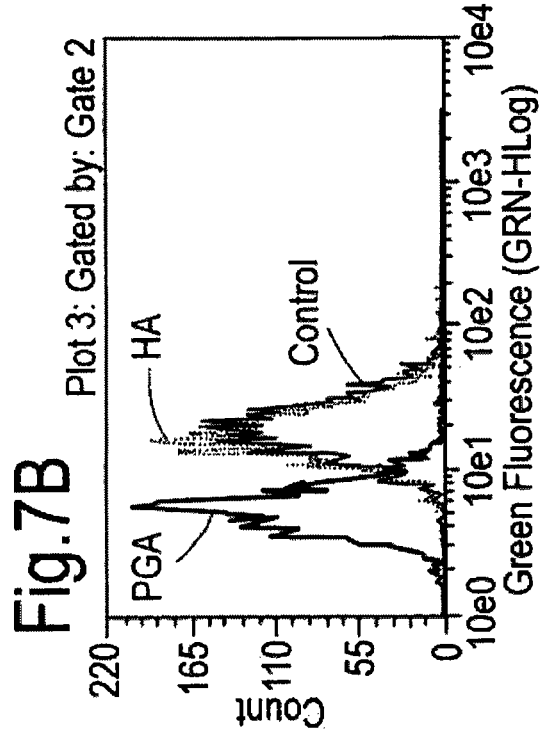
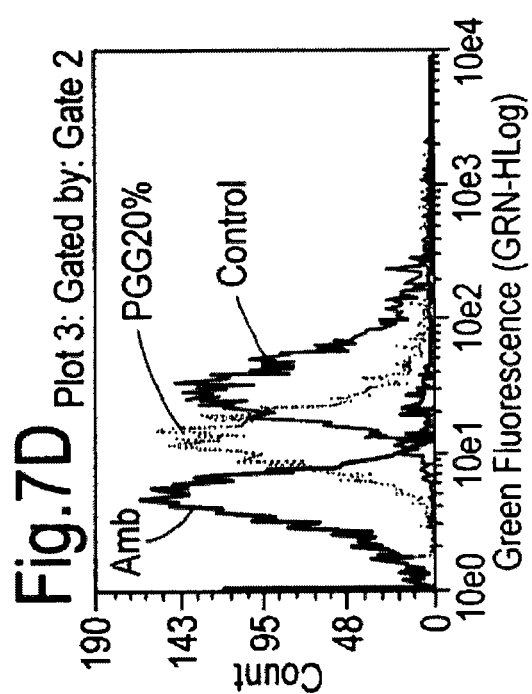
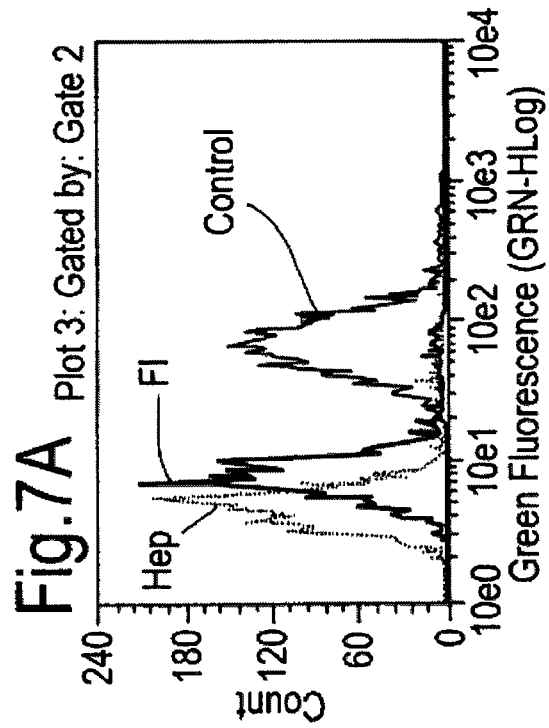
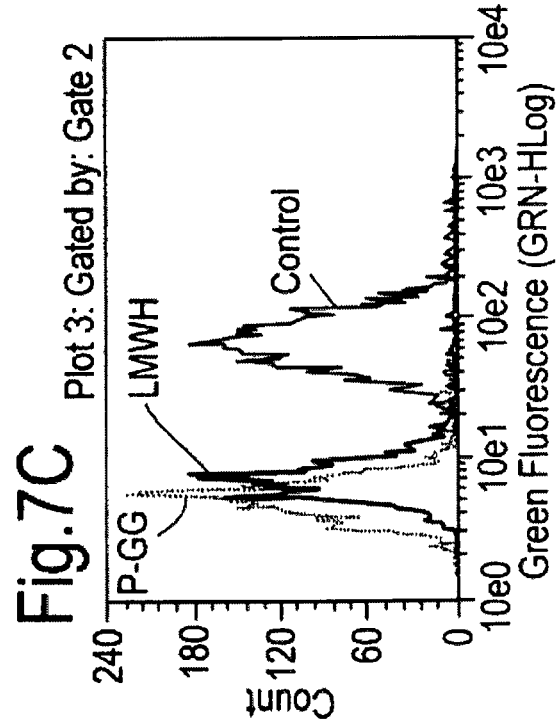

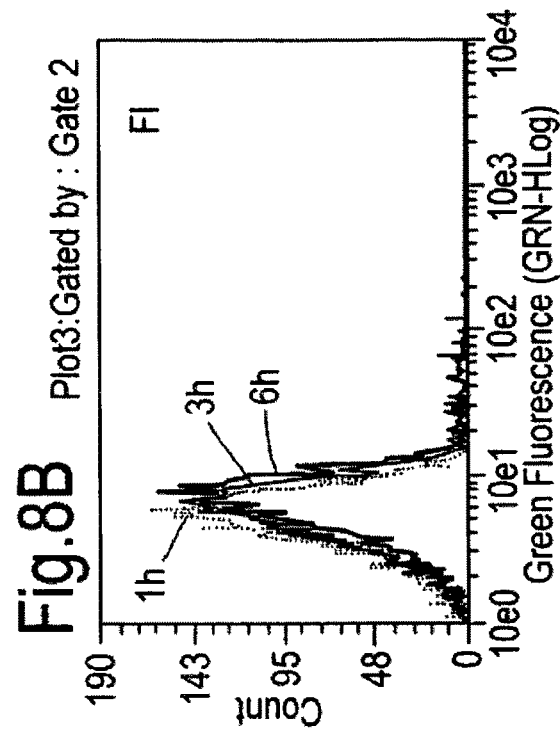
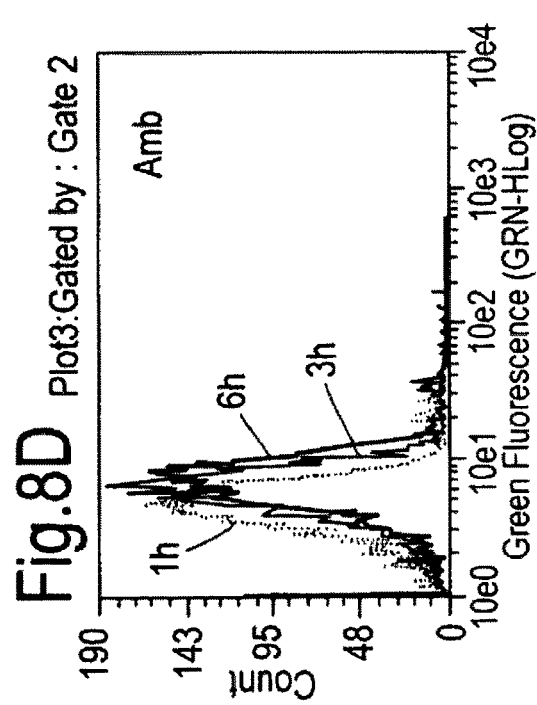
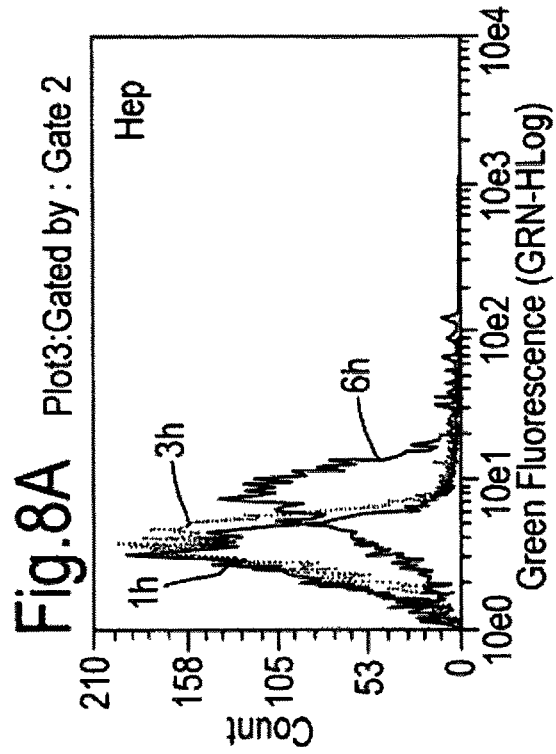
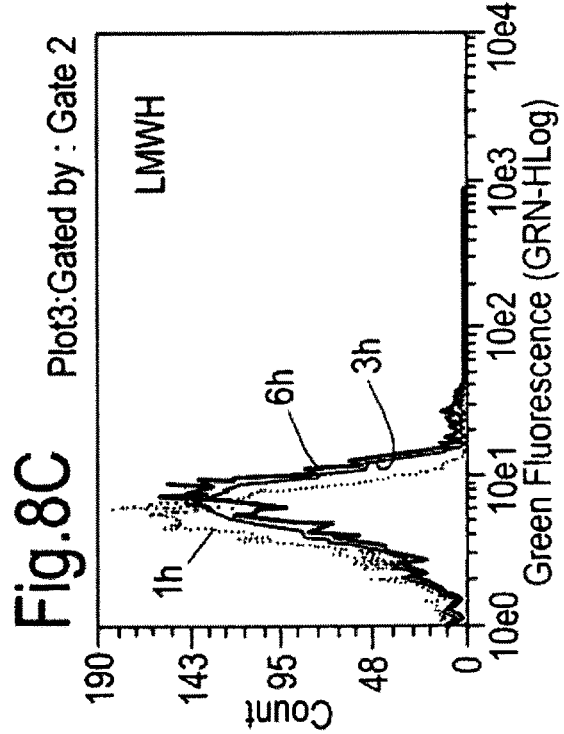

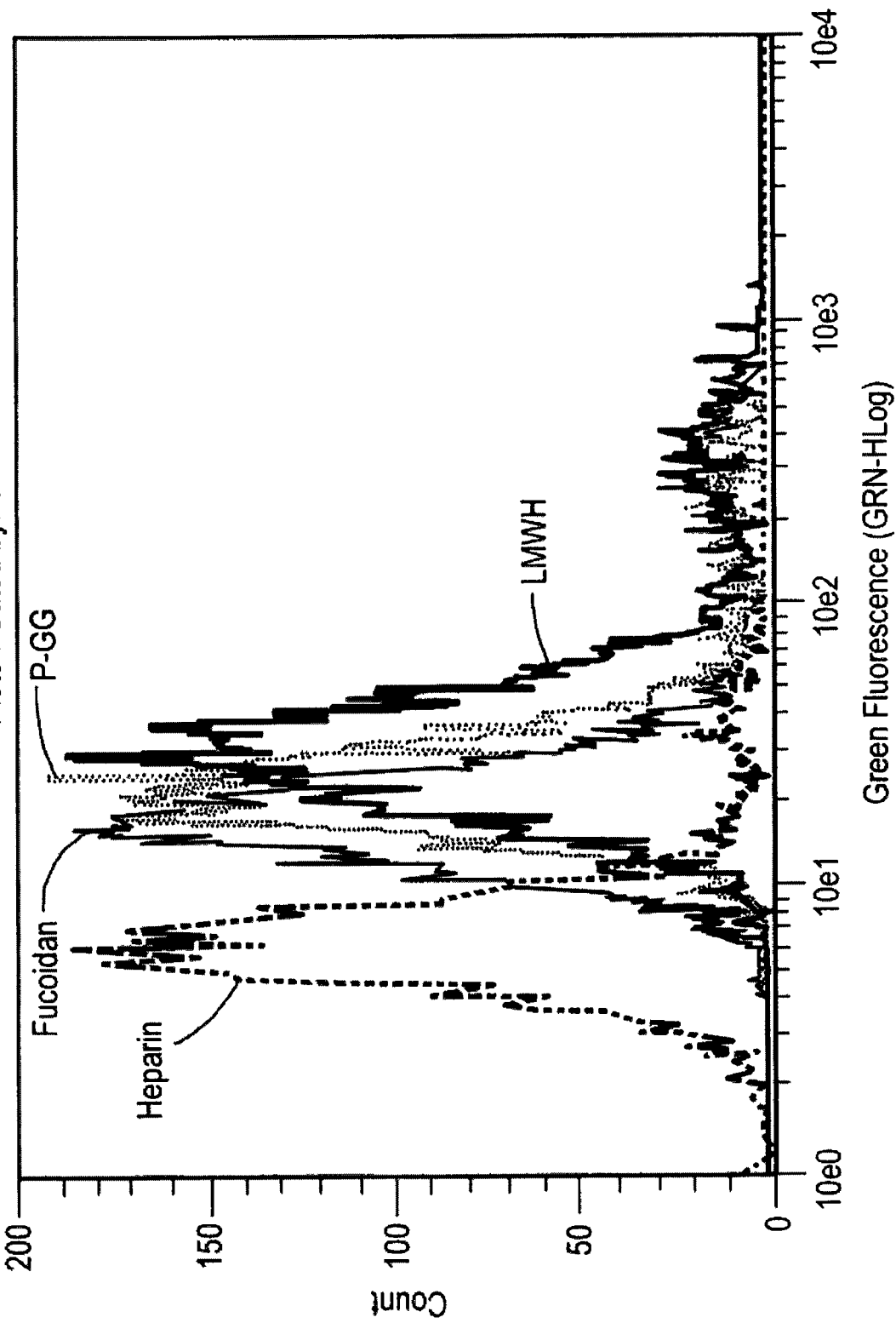

SEQUENCE LISTING

```
<160> NUMBER OF SEQ ID NOS: 6

<210> SEQ ID NO 1
<211> LENGTH: 7
<212> TYPE: PRT
<213> ORGANISM: Drosophila melanogaster

<400> SEQUENCE: 1

Arg Arg Met Lys Trp Lys Lys
1               5

<210> SEQ ID NO 2
<211> LENGTH: 34
<212> TYPE: PRT
<213> ORGANISM: Herpes simplex virus type 1

<400> SEQUENCE: 2

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 3
<211> LENGTH: 26
<212> TYPE: PRT
<213> ORGANISM: Artificial Sequence
<220> FEATURE:
<223> OTHER INFORMATION: Chimeric Protein

<400> SEQUENCE: 3

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 4
<211> LENGTH: 11
<212> TYPE: PRT
<213> ORGANISM: Human immunodeficiency virus

<400> SEQUENCE: 4

Tyr Gly Arg Lys Lys Arg Arg Gln Arg Arg Arg
1               5                   10
```

```
<210> SEQ ID NO 5
<211> LENGTH: 7
<212> TYPE: PRT
<213> ORGANISM: Homo sapiens

<400> SEQUENCE: 5

Lys Leu Ala Lys Leu Ala Lys
1               5

<210> SEQ ID NO 6
<211> LENGTH: 11
<212> TYPE: PRT
<213> ORGANISM: Artificial Sequence
<220> FEATURE:
<223> OTHER INFORMATION: CPP with 3 Mtt-protected Lys
<220> FEATURE:
<221> NAME/KEY: X
<222> LOCATION: (1)..(11)
<223> OTHER INFORMATION: X provides for Mtt-protected Lys

<400> SEQUENCE: 6

Lys Arg Arg Met Lys Xaa Trp Lys Xaa Lys Xaa
1               5                   10
```

CAGED CELL PENETRATING PEPTIDE-POLYMER CONJUGATES FOR DIAGNOSTIC AND THERAPEUTIC APPLICATIONS

CROSS-REFERENCE TO RELATED APPLICATIONS

This application is a continuation application of U.S. application Ser. No. 13/700,847, filed on Oct. 1, 2013, which is a U.S. National Phase application, filed under 35 U.S.C. § 371, of International Application No. PCT/IL2011/000413, filed on May 26, 2011, which claims priority to, and the benefit of, U.S. Provisional Application No. 61/349,819, filed on May 29, 2010, the entire contents of which are incorporated herein by reference in their entireties.

INCORPORATION-BY-REFERENCE OF SEQUENCE LISTING

The contents of the file named "WOLF-003C01US_ST25.txt", which was created on Nov. 30, 2018, and is 1.86 KB in size are hereby incorporated by reference in their entirety.

FIELD OF THE INVENTION

This invention describes a targeting strategy for the selective intracellular delivery of diagnostic or therapeutic agents to cells by means of polymer-caged cell penetrating peptide conjugates modified to include a diagnostic or therapeutic agent, which enhances the sensitivity of the diagnostic and therapeutic agent.

BACKGROUND OF THE INVENTION

The development of therapeutic agents capable of specifically targeting cancer cells and tumor-associated microenvironments including tumor blood vessels remains an important goal.

One strategy to achieve a high local concentration of chemotherapeutic drugs in tumor tissues is the incorporation of a targeting ligand able to actively guide the therapeutic agents to antigens or receptors uniquely expressed or over-expressed on the target cells relative to normal tissues. Various targeted drug delivery systems have been designed to contain antibodies or antibody Fab' fragments, lectins, proteins or peptides as targeting ligands to direct chemotherapeutic drugs selectively to cancer cells. However, when constructing targeted drug delivery systems, issues of the degree of receptor expression, heterogeneity in receptor expression among different tumor cells, binding affinity of the ligands for their receptor and the occurrence of receptor-mediated internalization might limit the choice of targeting ligands that are available for active drug targeting.

Certain polycationic sequences [also termed cell-penetrating peptides (CPPs) or protein transduction domains (PTDs)] can bring covalently attached payloads into mammalian cells without requiring specific receptors. Such proteins or peptides contain domains of less than 20 amino acids that are highly rich in basic residues, and have been used for intracellular delivery of various cargoes with molecular weights significantly greater than their own. These peptides include the 60 amino acid Antennapedia (Antp) (from *Drosophila*), the penetratin homeodomain derived peptide sequence (RRMKWKK (SEQ ID NO: 1) the HIV-1 Tat protein (TATp), The VP22 protein (DAATATRGRSAAS-RPTERPRAPARSASRPRRPVD (SEQ ID NO: 2) from the Herpes Simplex Virus type-1, the chimeric peptides such as transportan (GWTLNSAGYLLKINLKALAA1AKKIL (SEQ ID NO: 3)), and synthetic polyarginines, such as R9.

However, several biologic features limit CPP usefulness in living animals, most significantly being the lack of cell specificity. All the CPPs are highly positively charged, presenting basic residues of lysine or arginine. These cationic oligopeptides are able to attach rapidly and strongly to the cell surface through non-specific electrostatic interactions with the negative charges present of anionic phospholipids and glycosaminoglycans. In fact, upon administration (intravenous, IV, or intraperitoneal, IP), CPPs and their therapeutic conjugates are dispersed almost all over the body and can be found in blood cells, lung, liver, kidney and other tissues, even in the brain, indicating the penetration through the blood brain barrier (BBB). Therefore in drug delivery systems (DDS) the use of conventional CPPs was generally limited by the nature of the cargo molecule and its ability to keep healthy cells unharmed due to non-specific cell penetration.

While some efforts were made to enhance cell uptake specificity, including fusing the CPP to a cleavable linker, which prevents uptake unless cleavage occurs, such systems are not terribly versatile or reliable.

There remains a need for effective targeting of diseased cells and tissue and thereby effective diagnostic and therapeutic targeted delivery systems of high sensitivity.

SUMMARY OF THE INVENTION

In one embodiment this invention provides a caged cell penetrating peptide (cCPP)-macromolecular carrier conjugate characterized by the structure of formula 1:

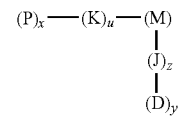

wherein
x and y indicate percentages of the respective element composition of the conjugate,
wherein x is between about 0.05%-50%, y is between 0 to 50, u is between 0-50% and z is between 0-50%;
P is a caged cell penetrating peptide
M is a macromolecular carrier molecule;
D is a detectable agent or a therapeutic agent, or a combination thereof; and
J and K are spacer molecules.

In some embodiments, the invention also provides a composition comprising a conjugate as herein described.

In other embodiments, the invention provides a method of imaging an inflammatory condition in a subject, said method comprising administering a conjugate of the invention to said subject.

In another embodiment, the invention provides a method of imaging a disease associated with neovascularization in a subject, said method comprising administering a conjugate of this the invention to said subject.

In another embodiment, this invention provides a method of imaging a cancerous cell or cancerous tissue in a subject, said method comprising the step of contacting said cancer or cancerous tissue with a conjugate of this invention.

In another embodiment, this invention provides a method of treating an inflammatory condition in a subject, said method comprising administering a conjugate of this invention to said subject.

In another embodiment, this invention provides a method of treating a disease associated with neovascularization in a subject, said method comprising administering a conjugate of this invention to said subject.

In another embodiment, this invention provides a method of treating a cancerous cell or cancerous tissue in a subject, said method comprising the step of contacting said cancer or cancerous tissue with a conjugate of this invention.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3A depicts the structure of a FITC-labeled HPMA copolymer, M-cCPP-FITC. FIG. 3B depicts the structure of a HPMA-bearing pro-apoptic peptide linked via pH sensitive bond, M-(cCPP)-KLAK.

FIG. 4A depicts light activated cell penetration of M-(cCPP)-FITC in PC-3 cells. FIG. 4B depicts light activated cell penetration of M-(cCPP)-FITC in 3LL cells. FIG. 4C depicts light activated cell penetration of M-(cCPP)-FITC in A-431 cells. FIG. 4D depicts light activated cell penetration of M-(cCPP)-FITC in SW-480 cells.

FIG. 5A depicts LysoTracker Red staining in illuminated cells. FIG. 5B depicts FITC staining in illuminated cells. FIG. 5C depicts a merged image of LysoTracker Red staining and FITC staining in illuminated cells. FIG. 5D depicts LysoTracker Red staining in non-illuminated cells. FIG. 5E depicts FITC staining in non-illuminated cells. FIG. 5F depicts a merged image of LysoTracker Red staining and FITC staining in non-illuminated cells.

FIG. 6A depicts illumination time-dependence and dose-dependence of the viability of PC-3 cells incubated with 80 μM (solid blue), 40 μM (dashed blue), 20 μM (dots blue) M-(cCPP)-KLAK (KLAK equiv), 80 μM KLAK (solid green), and 80 μM M-(cCPP) (solid red), as determined by MIT assay. The results presented are the average of 3 independent experiments, in duplicates. Untreated control cells corresponded to 100% viability. FIG. 6B depicts light-induced cell cytotoxicity of polymer-KLAK conjugates and free KLAK against various cell-types including A431 cells (top left graph), PC-3 cells (top right graph), 3LL cells (bottom left graph) and SW480 cells (bottom right graph). Cells were incubated with 60 μM KLAK equivalent M-(cCPP)-KLAK (dark column), M-(cCPP) (gray column) or 60 μM KLAK (white column) and were illuminated immediately with UV light (365 nm) for 8 minutes followed by 2 hours incubation at 37° C. Cell viability was analyzed by MIT assay.

FIG. 7A-FIG. 7D depict FACS analysis results of B-16 cells incubated with HPMA-CPP-FITC conjugate mixed with different polyanions (Hep, FI, PGA, HA, P-GG, LMWH, Amb) for 10 min, and then added to B16-cell monolayers. Control cells were treated with HPMA-CPP-FITC conjugate only. FIG. 7A depicts results of B-16 cells incubated with HPMA-CPP-FITC conjugate mixed with Hep or FI. FIG. 7B depicts results of B-16 cells incubated with HPMA-CPP-FITC conjugate mixed with PGA or HA. FIG. 7C depicts results of B-16 cells incubated with HPMA-CPP-FITC conjugate mixed with P-GG or LMWH. FIG. 7D depicts results of B-16 cells incubated with HPMA-CPP-FITC conjugate mixed with Amb. The mean fluorescence intensity was significantly reduced following pre-treatment with Hep, LMWH, FI, PGA, PGG, and Amb, due to the efficient masking of the CPP activity FIG. 8A-FIG. 8D depict FACS analysis results of stability testing of HPMA-CPP-FITC polyanion complexes incubated with B-16 cells at different time points. FIG. 8A depicts results of B-16 cells incubated with a complex of HPMA-CPP-FITC and the polyanion Hep. FIG. 8B depicts results of B-16 cells incubated with a complex of HPMA-CPP-FITC and the polyanion FI. FIG. 8C depicts results of B-16 cells incubated with a complex of HPMA-CPP-FITC and the polyanion LMWH. FIG. 8D depicts results of B-16 cells incubated with a complex of HPMA-CPP-FITC and the polyanion Amb. The mean fluorescence intensity was significantly reduced following pretreatment with the complexes, indicating that complexes were stable at growth medium for at least 6 hours.

FIG. 9A depicts the reversible masking of CCP activity by polyanion complexes comprising the polyanion fucoidan via the addition or protamine. FIG. 9B depicts the reversible masking of CCP activity by polyanion complexes comprising the polyanion LMWH via the addition or protamine. FIG. 9C depicts the reversible masking of CCP activity by polyanion complexes comprising the polyanion Heparin via the addition or protamine. FIG. 9D depicts the reversible masking of CCP activity by polyanion complexes comprising the polyanion P-GG-OH via the addition or protamine.

FIG. 10 depicts FACS analysis results of polyanion release from HPMA-CPP-FITC complexes by protamine was at the following order: LMWH>P-GG100%>Fl>Hep.

Figure 1:
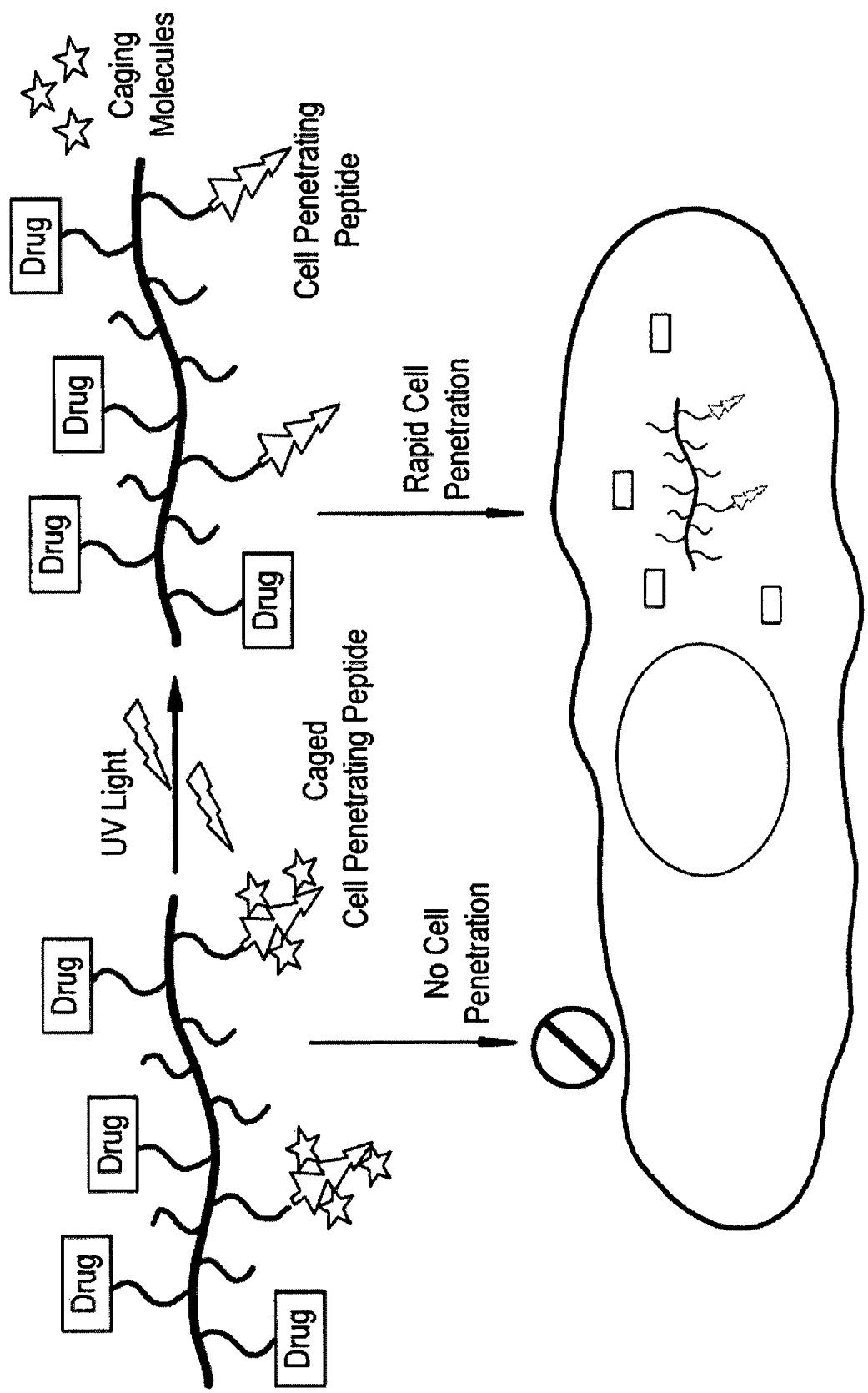
FIG. 1 depicts a scheme for light activated cell penetration of polymer-cCPP conjugates. In dark, the copolymer bearing cCPP is inactive and cannot cross the cell membrane. Upon illumination with UV light the caging molecule is released, cell penetration ability is restored and the copolymer can rapidly enter cells.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, inter alia, for the specific intracellular uptake of imaging and therapeutic agents.

In one embodiment this invention provides a caged cell penetrating peptide (cCPP)-macromolecular carrier conjugate characterized by the structure of formula 1:

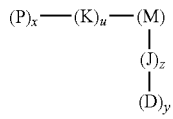

wherein
x and y indicate percentages of the respective element composition of the conjugate,
wherein x is between about 0.05%-50%, y is between 0 to 50, u is between 0-50% and z is between 0-50%;
P is a caged cell penetrating peptide
M is a macromolecular carrier molecule;
D is a detectable agent or a therapeutic agent, or a combination thereof; and
J and K are spacer molecules.

The improved selective targeting and uptake of therapeutic conjugates into, inter alia tumors is an application of the invention described herein. Caged peptides (cCPP) have been utilized to promote light-dependent intracellular delivery of macromolecules and site specific drug release.

In one embodiment of the invention, and as exemplified herein, some embodiments of the conjugates as herein described allowed for light stimuli to control the function of CPPs and thus improved the efficiency and selectivity in a model drug delivery system to target cells.

In some embodiments, such light-induced delivery serves as an ideal external trigger signal, since it can be manipulated very precisely, for example via laser and other appropriate methodology as will be appreciated by the skilled artisan, resulting in a rapid increase in the concentration of drug molecules taken up within a given cell.

One unexpectedly useful embodied advantage of the cCPP-based drug delivery systems of this invention is that it allows for very efficient cellular penetration without the need for receptor mediated uptake (100% of the treated cells demonstrated uptake within 2 hours, as exemplified herein).

Another unexpectedly useful embodied advantage of the cCPP-based delivery systems, according to this aspect, is that the absence of need for a specific cell receptor to mediate uptake provides for the further ability, upon light illumination of the cancerous tissue, to also target uptake within nearby cells at the tumor microenvironment, resulting in a local toxicity that could kill cancer cells, as well as supporting endothelial cells and stromal cells within the tumor microenvironment.

Another unexpectedly useful embodied advantage of the cCPP-based delivery systems, is that the cCPP-based delivery system results in cargo delivery not just to the surface of the target cell but rather intracellularly and within the nucleus, as well, which is important for therapeutic payloads for in vivo drug and gene delivery.

The cCPP-based delivery systems of this invention, also referred to herein as the conjugates of this invention, comprise a caged cell penetrating peptide (cCPP)-macromolecular carrier conjugate.

Examples of caged cell penetrating peptides include any such peptide known in the art, for example, the TAT protein, which is a transcription factor of human immunodeficiency virus-1, HIV-I) and protein fragments thereof, such as amino acids 47 to 57 (YGRKKRRQRRR (SEQ ID NO: 4), (Fawell, S. et al, Proc. Natl. Acad. ScL USA, 91:664, 1994). Other examples of cell penetrating peptides (CPPs) include a peptide having an amino acid sequence consisting of amino acids 267 to 300 of the VP22 protein of HSY-I (herpes simplex virus type 1) (Elliott, G. et al, Cell, 88:223, 1997), a peptide having an amino acid sequence consisting of amino acids 84 to 92 of the UL-56 protein of HSV-2 (GenBank code:D1047 gi:221784) and a peptide having an amino acid sequence consisting of amino acids 339 to 355 of the antennapedia (ANTP) protein of *Drosophila* sp. (Schwarze, S. R. et al, Trends. Pharmacol ScL, 21:45, 2000). In addition, artificial peptides consisting of positively charged amino acids were also found to be effective (Laus R. et al., Nature Biotechnol. 18:1269-1272 (2000)). Another example of a CPP is penetratin, as described and exemplified herein, or CPP as described in U.S. Pat. No. 7,579,318; U.S. Patent Application Publication No. 20100048487; U.S. Patent Application Publication No. 20090292003; Mae M. et. al., Current Opinion in Pharmacology Volume 6: Pages 509-514 (2006); U.S. Patent Application Publication No. 20100061932A1; PCT International Patent Application Publication No. WO 2009/120396; U.S. Patent Application Publication No. 20090292003A1; U.S. Patent Application Publication No. 20080234183, and others, as will be appreciated by the skilled artisan.

The cell penetrating peptides which comprise a part of the conjugates of this invention are caged. The term "caged" refers, in some embodiments, to an association of the indicated peptide with a protecting group, which group renders the CPP activity inactive, until such time as the CPP is liberated from the protecting group. In some embodiments, caging is via a photolabile protecting group, whereby following illumination of the cCPP, the molecule is irreversibly activated, since the photolabile group is removed from the CPP.

In some embodiments, the photoprotecting group may be any appropriate group as known in the art, for example, a 4,5-Dimethoxy-2-nitrobenzyl chloroformate (Nvoc) protecting group, as described and exemplified herein, or a protecting group as described in WO9410128, Michiko Iwamura et al., (1991) Synlett 35-36; Reichmanis et al., J. Polymer Sc. Polymer Chem. Ed. 23:1-8 (1985) McCray et al., Annu. Rev. Biophys. Biophys. Chem. 18:239-70 (1989); A. Barltrop et al., Chemical Communications, p. 822 (Nov. 22, 1966); Wilcox et al., J. Org. Chem. 55:1585-1589 (1990); U.S. Pat. No. 5,489,678; PCT International Patent Application Publication No. WO 94/10128, or Nitrovera trylchloroformate; Ru(bpy)2Cl2 (see for example, Watai, Y.; Sase, I.; Shiono, H.; Nakano, Y. FEBS Lett 2001, 488, 39-44; Tatsu, Y.; Shigeri, Y.; Ishida, A.; Kameshita, I.; Fujisawa, H.; Yumoto, N. Bioorg Med Chem Lett 1999, 9, 1093-6; Fino, E.; Araya, R.; Peterka, D. S.; Salierno, M.; Etchenique, R.; Yuste, R. Front Neural Circuits 2009, 3, 2) and others, as will be appreciated by the skilled artisan.

In some embodiments the photo-cleavable caging molecules may comprise Nitro benzylchloroformate, diethylamino-coumarin-4-yl; Ruthenium complexes, such as Ru(bpy)2Py2 or Ru(bpy)2Cl2, and others as will be appreciated by the skilled artisan.

In some embodiments, caging is via a time-released protecting group, whereby over time the protecting group is removed from the CPP.

In some embodiments, the time-released protecting group comprises any appropriate group known in the art, for example, 1,2 cyclohexanedione, 2,3 butanedione, Phenylglyoxal or glyoxal (see for example, Toi, K.; Bynum, E.; Norris, E.; Itano, H. A. Chemical Modification of Arginine with 1,2-Cyclohexanedione. J Biol Chem 1965, 240, PC3455-7; ankeelov, J. A., Jr. Modification of arginine in proteins by oligomers of 2,3-butanedione. Biochemistry 1970, 9, 2433-9; Takahashi, K. The reaction of phenylglyoxal with arginine residues in proteins. J Biol Chem 1968, 243, 6171-9).

In some embodiments, caging is via a pH-dependent protecting group, whereby when the pH changes the protecting group is removed from the CPP.

In some embodiments, the pH-dependent protecting group comprises any appropriate group known in the art, for example, Citraconic anhydride, Maleic anhydride and others (see for example, Brinegar, A. C.; Kinsella, J. E. J Agric Food Chem 1980, 28, 818-24).

The cCPP is associated with or attached to a macromolecular carrier molecule. In some embodiments, the macromolecular carrier is a polymer, micelle, polymer micelle, microparticles, nanoparticle, liposome, dendrimer or a bead. It is to be understood, in this context, that in the formula:

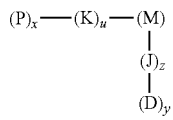

the presence of the "-" represents a covalent or non-covalent association between the thus-joined moieties, i.e. between the cCPP and the macromolecular carrier or between the cCPP and spacer and/or spacer and macromolecular carrier, or between the detectable or therapeutic agent and the molecular carrier and/or between the detectable or therapeutic agent and spacer and/or spacer and molecular carrier.

In some embodiments, the polymer may comprise underivatized or derivatized monomers of N-(2-hydroxypropyl)methacrylamide (HPMA), N-methylacrylamide, N,N-dialkylacrylamides, acrylic acid, methacrylic acid, polyamino acids, polysaccharides, polymers containing polyethyleneoxide sequences and polyvinyl pyrrolidonemaleic anhydride polymers, polylactic-co-glycolic acid, or any copolymer thereof. In some embodiments, the macromolecular carrier is a dendrimers, In some embodiments, the polymer may comprise a polymethylmethacrylate (PMMA), acrylics, acrylates, polyethylene, polyethylene terephthalate, polycarbonate, polystyrene and other styrene polymers, polypropylene, polytetrafluoroethylene. In one embodiment, the polymers are homo- or, in another embodiment heteropolymers. In another embodiment, the polymers are synthetic, or, in another embodiment, the polymers are natural polymers. In another embodiment, the polymers are free radical polymers, or, in another embodiment, graft polymers. In one embodiment, the polymers may comprise proteins, peptides or nucleic acids.

Synthesis of the polymer precursors or of the polymers of this invention may be carried out in a number of representative suitable solvents including, water, anhydrous polar aprotic solvents such as acetonitrile, tetrahydrofuran, dioxane, or the like, halogenated solvents such as chloroform, or the like. In some embodiments, synthesis is conducted as exemplified herein, or as a variation thereof, as will be appreciated by the skilled artisan. Synthesis of the monomeric units of the polymers and their linkage to other monomeric units are understood to reflect the choice of monomeric unit and can be accomplished by routine methodology known in the art.

In another embodiment, the polymers are synthesized enzymatically. In one embodiment, the enzymes used to synthesize the polymers of this invention comprise lipases, such as, for example *Candida antarctica* lipase, or in another embodiment, lipase A, or in another embodiment, lipase B. In another embodiment, the enzyme may comprise an esterase, or in another embodiment, a protease, such as, for example papain or chymotrypsin. In one embodiment, molecular weight of the hydrophilic units is chosen such that its ability to affect polymerization is considered. In one embodiment, the polymer is functionalized with for example, an alkyl group of varying chain length, comprising a polar functionality at the end of the chain.

[Polymers obtained by methods as described herein can be characterized by methods well known in the art. For example, the molecular weight and molecular weight distributions can be determined by gel permeation chromatography (GPC), matrix assisted laser desorption ionization (MALDI), and static or dynamic light scattering. Physical and thermal properties of the polymer products can be evaluated by thermal gravemetric analysis (TGA), differential scanning calorimetry (DSC), or surface tensiometer; the chemical structures of the polymers can be determined by, e.g., NMR (1H, 13C NMR, 1H-1H correlation, or 1H-13C correlation), IR, UV, Gas Chromatography-Electron Impact Mass Spectroscopy (GC-EIMS), EIMS, or Liquid Chromatography Mass Spectroscopy (LCMS).

In some embodiments, the macromolecular carrier is a bead, which may comprise magnetic or non-magnetic beads, which may further be functionalized in order to associate the cCPP therewith, e.g. by incorporating divinyl sulfone activated polysaccharides, polystyrene beads that have been functionalized with tosyl-activated esters, magnetic polystyrene beads functionalized with tosyl-activated esters, and others. Beads may be made of sepharose, sephacryl, polystyrene, agarose, polysaccharide, polycarbamate or any other kind of beads that can be suspended in aqueous buffer.

In some embodiments, the macromolecular carrier is a liposome, which may be any appropriate liposome as known in the art, for example as described in U.S. Pat. Nos. 6,645,463; 5,885,613; 5,820,873, PCT International Patent Applications Publication Nos. WO97/38010, and WO 96/34598, and others, as will be appreciated by the skilled artisan.

In some embodiments, the macromolecular carrier is a micelle, which may be. any appropriate niicelle as known in the art, for example, as described in PCT International Patent Applications Publication Nos. WO 03/047494; WO 03/047493; WO 99/60169; WO 00/44348; WO 98/10798; WO 97/48337, and others, as will be appreciated by the skilled artisan.

In some embodiments, the macromolecular carrier is a nanoparticle, which may be any appropriate nanoparticle as known in the art, for example, as described in PCT International Patent Applications Publication Nos. WO 10/048623; WO 10/009146; WO 09/098510; WO2009081287; U.S. Patent Application Publication No. 20090028948; and others, as will be appreciated by the skilled artisan.

In some embodiments, the macromolecular carrier is a dendrimer, which may be any appropriate dendrimer known in the art, for example, as described in US Patent Application Publication No. 20050271615; 20030077635; 20050085417; PCT International Application Publication No. WO 04/041310; WO 04/019993; WO 05/040094; WO 02/26867, and others, as will be appreciated by the skilled artisan.

In some embodiments, the macromolecular carrier is also further associated with or bound to a detectable agent, or in other embodiments, the macromolecular carrier is also further associated with or bound to a therapeutic agent.

In some embodiments, according to this aspect, the detectable agent is fluorescent, luminescent or electron dense.

In some embodiments, the detectable agent is FITC, DAPI, Cy3, Cy3.5, Cy5, Cy5. 5, Cy7, GFP, BFP or RFP, or variants thereof, indocyanine green (ICG), or 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide (IR783), gadolinium, $^{19}F$.

In some embodiments, the therapeutic agent is a toxin, a chemotherapeutic agent, a radioisotope, an antimetabolite, a microtubule inhibitor, or a combination thereof.

In some embodiments, the therapeutic agent is an antineoplastic agent such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chiorambucil, meiphalan (e.g., PAM, L-PAM or phenylalanine mustard), mercaptopurine, rnitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparagmase, interferona-2a, interferona-2b, teniposide (VM-26), vinbiastine sulfate (VLB), vincristine sulfate, bleomycin sulfate, hydroxyurea, procarbazine, and dacarbazine; mitotic inhibitors such as etoposide, coichicine, and the ymca alkaloids, radiopharmaceuticals such as radioactive iodine and phosphorus products and others as will be appreciated by the skilled artisan.

In one embodiment, the term "therapeutic", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent.

In some embodiments, the therapeutic protein ameliorates, abrogates or diminishes pathogenesis of a disease in a subject, or in some embodiments, improves symptoms of a disease in a subject, or treats, delays progression of, prolongs remission of, or reduces the incidence or severity of an indicated disease or condition in the subject.

In one embodiment, the term "toxin" refers to a molecule which results in toxic effects in cells and/or tissue exposed to the toxin. In one embodiment, the toxin results in cell death, or in another embodiment, cell damage. In one embodiment, the toxin is a natural product of cells, such as bacterial cells, wherein the toxin is used, in one embodiment, when specifically targeted to disease cells as a means of selective cell killing of diseased cells. In one embodiment, the toxin may comprise any known in the art, such as, for example that produced by cholera, tetanus, or any other appropriate species, as will be appreciated by one skilled in the art.

In another embodiment, this invention also comprises incorporation of any toxic substance for therapeutic purpose. In one embodiment, the conjugates of this invention may incorporate an oligonucleotide encoding a suicide gene, which when taken up within diseased cells or tissue, or neighboring cells or tissue thereto, is expressed within such cells.

In one embodiment, the term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. In one embodiment, the term "prodrug" means any compound that can be converted to a toxic product for cells. Representative examples of such a prodrug is gancyclovir which is converted in vivo to a toxic compound by HSV-thymidine kinase. The gancyclovir derivative subsequently is toxic to cells. Other representative examples of prodrugs include acyclovir, FJAU, 1-(2-deoxy-2-fluoro-B-D-arabinofuranosyl)-5-iodouracil, 6-methoxypurine arabinoside for VZV-TK, and 5-fluorocytosine for cytosine deaminase.

In some embodiments, the detectable or therapeutic agent is bound to the polymers in the conjugates of this invention indirectly, via a spacer molecule.

In one embodiment, the spacer is selected depending upon the properties desired. For example, the length of the spacer can be chosen to optimize the kinetics and specificity of binding, including any conformational changes induced by binding of the CPP to a target cell. The spacer, in some embodiments, should be long enough and flexible enough to allow the, e.g. CPP and the target cell to freely interact/allow for intake of the CPP. In some embodiments, if the spacer is too short or too stiff, there may be steric hindrance between the conjugate and the cell.

In some embodiments, the spacer can be, using numerous protocols known in the art, such as those described in, for example, Pierce Chemicals "Solutions, Cross-linking of Proteins: Basic Concepts and Strategies," Seminar #12, Rockford, Ill., and modifications of such methods may be readily achieved, as will be appreciated by the skilled artisan.

In some embodiments, several linkers may be included in order to take advantage of desired properties of each linker. Chemical linkers and peptide linkers may be inserted by covalently coupling the linker to the detectable agent or therapeutic agent, for example. Heterobifunctional agents may be used to effect such covalent coupling. Peptide linkers may also be used. Flexible linkers are contemplated for use, either alone or with other linkers are also contemplated herein.

In some embodiments, cleavable spacers are used. Heterobifunctional cleavable cross-linkers may comprise N-succinimidyl (4-iodoacetyl)-aminobenzoate; sulfosuccinimydil (4-iodoacetyl)-aminobenzoate; 4-succinimidyl-oxycarbonyl-a-(2-pyridyidithio)-toluene; sulfosuccinimidyl-6-[a-methyl-a-(pyridyidithiol)-toluamido]hexanoate; N-succinimidyl-3-(-2-pyridyldithio)-proprionate; succinimidyl 6(3(-(-2-pyridyidithio)-proprionamido]hexanoate; sulfosuccinimidyl 6(3(-(-2-pyridyidithio)-propionamido]hexanoate; 3-(2-pyridyidithio)-propionyl hydrazide, Ellman's reagent, dichlorotriazinic acid, S-(2-thiopyridyl)-L-cysteine. Further exemplary bifunctional spacers are disclosed in U.S. Pat. Nos. 5,349,066. 5,618,528, 4,569,789, 4,952,394, and 5,137,877.

The term linker and spacer may, in some embodiments, be considered to be synonymous.

Acid cleavable spacers, photocleavable and heat sensitive spacers may also be used, particularly where it may be necessary to cleave the targeted agent to permit it to be more readily accessible to reaction. Acid cleavable linkers/spacers include, but are not limited to, bismaleimideothoxy propane; and adipic acid dihydrazide linkers (see, e.g., Fattom et al. (1992) Infection &Immun. 60:584-589) and acid labile transferrin conjugates that contain a sufficient portion of transferrin to permit entry into the intracellular transferrin cycling pathway (see, e.g., Welhner et al. (1991) J. Biol. Chem. 266:4309-4314). Such acid cleavable spacers and heat sensitive spacers are useful in connection with caging the peptides, as described further.

Photocleavable linkers are linkers that are cleaved upon exposure to light (see, e.g., Goldmacher et al. (1992) Bioconj. Chem. 3:104-107, which linkers are herein incorporated by reference), thereby releasing the targeted agent upon exposure to light. Photocleavable linkers that are cleaved upon exposure to light are known (see, e.g., Hazum et al. (1981) in Pept., Proc. Eur. Pept. Symp., 16th, Brunfeldt, K (Ed), pp. 105-110, which describes the use of a nitrobenzyl group as a photocleavable protective group for cysteine; Yen et al. (1989) Makromol. Chem 190:69-82, which describes water soluble photocleavable polymers, including hydroxypropylmethacrylamide polymer, glycine polymer, fluorescein polymer and methylrhodamine polymer; Goldmacher et al. (1992) Bioconj. Chem. 3:104-107, which describes a cross-linker and reagent that undergoes photolytic degradation upon exposure to near UV light (350 mn); and Senter et al. (1985) Photochem. Photobiol 42:231-237, which describes nitrobenzyloxycarbonyl chloride cross linking reagents that produce photocleavable linkages), thereby releasing the agent joined thereto upon exposure to light. Such photocleavable linkers are useful in connection with caging the peptides, as described further.

The conjugates of this invention are characterized by the structure of formula 1:

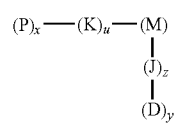

wherein P is a caged cell penetrating peptide, M is a macromolecular carrier molecule and D is a detectable agent or a therapeutic agent, and K and J are spacers, as described herein. According to this aspect, in certain embodiments of this invention, x, y, u and z indicate percentages of the respective element composition of the conjugate, wherein x is between about 0.05%-50%, y is between 0 to 50, u is between 0-50% and z is between 0-50%.

In some embodiments, as noted herein, the invention provides a method of imaging an inflammatory condition in a subject, said method comprising administering a conjugate of the invention to said subject.

In another embodiment, the invention provides a method of imaging a disease associated with neovascularization in a subject, said method comprising administering a conjugate of this the invention to said subject.

In another embodiment, this invention provides a method of imaging a cancerous cell or cancerous tissue in a subject, said method comprising the step of contacting said cancer or cancerous tissue with a conjugate of this invention.

In one embodiment imaging or detection is referred to as radiological. In one embodiment imaging or detection is done by means of an endoscope, for example, as described in Gahlen et al. (1999) J. Photochem. Photobiol. B. 52:131-5; Major et al., 1997, Gynecol. Oncol. 66:122-132, and others.

In one embodiment imaging or detection of the detectable moiety is accomplished by means of a catheter based device, including fiber optics devices, for example, as described in Teamey et al. 1997, Science 276: 2037-2039; Proc. Natl. Acad. Sci. USA 94:4256-4261.

In some embodiments, according to this aspect, uncaging of the CPP may be accomplished by the same means, via illumination at the appropriate site, using inter alia, such technologies.

In other embodiments, any appropriate imaging technology may be used, for example, phased array technology (Boas et al. 1994 Proc. Natl. Acad. Sci. USA 91: 4887-4891; Chance 1998, Ann. NY Acad. Sci. 838: 29-45), diffuse optical tomography (Cheng et al., 1998 Optics Express 3: 118-123; Siegel et al. 1999, Optics Express 4: 287-298), intravital microscopy (Dellian et al., 2000, Br. J. Cancer 82: 1513-1518; Monsky et al. 1999 Cancer Res. 59: 4129-4135; Fukumura et al. 1998, cell 94: 715-725) and confocal imaging (Korlach et al. Proc. Natl. Acad. Sci. USA 96: 8461-8466; Rajadhyaksha et al. 1995, J. Invest. Dermatol.

104: 946-952; Gonzalez et al. 1999, J. Med. 30: 337-356), and others as will be appreciated by the skilled artisan.

In one embodiment, the conjugates of this invention are useful in methods for the imaging of individual cells, a group of cells, a tissue, an organ or a combination thereof.

In one embodiment, imaging is accomplished with computed tomography, computed radiography, magnetic resonance imaging, fluorescence microscopy, angiography, arteriography, or a combination thereof.

In one embodiment, the imaging methods of this invention are conducted on a subject and in one embodiment, the subject has or is suspected of having cancer.

In one embodiment, the imaging methods as described herein may comprise near infrared fluorescence imaging. In one embodiment, an advantages of such optical imaging methods may include the use of non-ionizing low energy radiation, high sensitivity with the possibility of detecting micron-sized objects, continuous data acquisition, and the development of potentially cost-effective equipment. Optical imaging can be carried out at different resolutions and depth penetrations. Fluorescence-mediated tomography (FMT) can three-dimensionally localize and quantify fluorescent probes in deep tissues at high sensitivity. Several NIR fluorochromes have recently been coupled to affinity molecules (Becker, A., et al. Nature Biotechnology, 19: 327-331, 2001; Folli, S., et al Cancer Research, 54: 2643-2649, 1994, and can be adapted to comprise the polymers of this invention, as will be appreciated by one skilled in the art.

In one embodiment, the imaging methods as described herein may comprise nuclear imaging methods. Nuclear imaging is based on labeling molecules with a radioactive atom before their release in the system under study. Since photons of relatively high energy (>80 keV) can escape from the human body, it is possible to follow over time the 3D spatial distribution of the radioactive tracer through detection of the emitted radiation. A large variety of isotopes can be imaged. Their broadest classification is perhaps that in gamma and positron emitters: the former family is at the basis of single photon emission methods (such as planar scintigraphy and tomography, or SPECT), and the latter is used in Positron Emission Tomography (PET). Unlike in MRI or computed tomography (CT), the signal detected in nuclear imaging techniques is the radioactive emission of a single atom. Because these emissions are specific to the radioisotope used, and because it is possible with standard physics instrumentation to detect the emission of a single atom, nuclear imaging enjoys the advantages of both high specificity and sensitivity. Structural information, however, may be obtained only as far as the radiotracer redistributes following anatomical structures. Resolution of clinical scanners may be limited to about 5-6 mm for PET and ~1 cm for SPECT, thus, nuclear imaging methods are often used to complement the information provided by CT and/or MM scans in the context of multimodality imaging, and may be applied in this manner herein, representing an embodiment of this invention. In one embodiment, nuclear imaging is used in particular because of its sensitivity to extremely small quantities of matter. For example, it has recently been estimated that PET can detect as few as a cluster of 250 cells each bearing 30 Bq of 18F, which corresponds to 2.1 fg.

In another embodiment, different iodine isotopes can be chosen for radioactive labeling of compounds. In one embodiment, 123I, 125I and 131I can be used to obtain molecules with the same chemical and biological characteristics but different imaging and dosimetric properties.

In another embodiment, the conjugates of this invention allow for the combination of different imaging modalities. In one embodiment imaging comprises X-ray, MM, ultrasound or a combination thereof.

In another embodiment, this invention provides a method of treating an inflammatory condition in a subject, said method comprising administering a conjugate of this invention to said subject.

In another embodiment, this invention provides a method of treating a disease associated with neovascularization in a subject, said method comprising administering a conjugate of this invention to said subject.

In another embodiment, this invention provides a method of treating a cancerous cell or cancerous tissue in a subject, said method comprising the step of contacting said cancer or cancerous tissue with a conjugate of this invention.

In another embodiment, this invention provides for the use of a conjugate of this invention in the preparation of a medicament for use in treating an inflammatory condition in a subject.

In another embodiment, this invention provides for the use of a conjugate of this invention in the preparation of a medicament for use in treating a disease associated with neovascularization in a subject.

In another embodiment, this invention provides for the use of a conjugate of this invention in the preparation of a medicament for use in treating a cancerous cell or cancerous tissue in a subject.

In one embodiment, the term "treating" or "therapeutic agent" refers to curing a disease or being associated with the same. In another embodiment, "treating" or "therapeutic agent" refers to preventing a disease or being associated with the same. In another embodiment, "treating" or "therapeutic agent" refers to reducing the incidence of a disease, or being associated with the same. In another embodiment, "treating" or "therapeutic agent" refers to inducing remission, slowing the progression of a disease, "reducing", "suppressing" and "inhibiting" or lessening or decreasing the disease or symptoms thereof or being associated with the same. The term "progression" may refers to increasing in scope or severity, advancing, growing or becoming worse. The term "recurrence" refers, in one embodiment, to the return of a disease after a remission.

In one embodiment, the term "administering" refers to bringing a subject in contact with a nucleotide molecule of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

As exemplified herein, upon exposing the polymer-CPP conjugates to light, the conjugate penetration into target cells was enhanced, and such method promoted more effective intracellular delivery of the pro-apoptotic anticancer model drug, which demonstrates the efficacy of the conjugates of this invention in treating various diseases, as described herein.

Other methods caging of the CPP activity will be attained by the addition of counter ion (polyanion) to polymer-CPP conjugates.

Uncaging the CPP conjugates include the addition of polycations for polyanion-caged peptides.

In some embodiments, uncaging occurs following exposure to protamine. According to this aspect, and in some embodiments, the protamine is administered intravenously to a subject to promote uncaging. In some embodiments, caged HPMA-CPP-polyanion complexes are administered intraperitoneally (IP) and for uncaging, the Protamine is administered intravenously.

Caging via a time-released protecting group is exemplified herein, as well, which method may be another versatile means for regulated delivery of the conjugates of this invention.

In some embodiments, the methods of this invention serve as a general approach to promoting cellular cytotoxic effects, via use of the conjugates, which serves to promote specific intracellular uptake within the cell or tissue against which a cytotoxic response is desired.

In some embodiments, the conjugates/compositions and methods of this invention are useful in the diagnosis of any vascularized tumor, for example, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas).

In some embodiments, the conjugates/compositions and methods are useful in diagnosing other diseases associated with neovascularization, such as, but not limited to inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells Other angiogenesis-associated diseases or disorders which can be diagnosed and/or treated with the conjugates/ compositions or by the methods encompassed by the present invention include, but are not limited to, osteoarthritis, lupus, systemic lupus erythematosis, polyarteritis, artery occlusion, vein occlusion, carotid obstructive disease, sickle cell anemia, pseudoxanthoma elasticum, Paget's disease, lyme's disease, Best's disease, Eale's disease, Stargardt's disease, toxoplasmosis, phylectenulosis, lipid degeneration, chronic inflammation, atherosclerosis, hereditary diseases, such as Osler-Weber-Rendu disease.

Any number of assays may be utilized in order to verify that the drugs are delivered to the appropriate site, and are functional, and such assays will be tailored for the particular drug utilized and application evaluated.

Compositions

In one embodiment this invention provides a pharmaceutical composition comprising the conjugates of this invention.

In one embodiment the composition further comprising a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution or a suppository.

In one embodiment the composition is in a form suitable for oral, intravenous, intraarterial, intramuscular, intracranial, intranasal, subcutaneous, parenteral, transmucosal, transdermal, intratumoral or topical administration. In one embodiment the composition is a controlled release composition.

In one embodiment the composition is an immediate release composition. In one embodiment the composition is a liquid dosage form. In one embodiment the composition is a solid dosage form. In one embodiment the composition further comprises an antineoplastic compound, an immunotherapeutic agent or a drug.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The term "parenteral" administration as used herein refers to modes of administration which include intravenous, intramuscular, intraperitoneal, intrathecally, intrasternal, subcutaneous and intraarticular injection and infusion.

In one embodiment the composition can be administered to humans and other animals.

In one embodiment, either a composition suitable for imaging methods as herein described, or a composition incorporating a therapeutic agent may further comprise at least one antineoplastic compound, an immunotherapeutic agent or a drug.

In one embodiment, the compositions of this invention are biocompatible, and in another embodiment, may comprise pharmaceutically acceptable carriers or excipients, such as disclosed in Remington's Pharmaceutical Sciences, Mack Publishing Company, Easton, Pa., USA, 1985.

The conjugates of this invention may be used in the treatment or diagnosis of certain conditions such as in tagging, detecting or removing cancer cells These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the conjugates, it is desirable to slow the absorption of the same following its administration. This may be accomplished by the use of a liquid suspension of crystalline or amorphous material with poor water solubility. The rate of absorption of the drag then depends upon its rate of dissolution which, in turn, may depend upon crystal size and crystalline form.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Liquid dosage forms may include pharmaceutically acceptable emulsions, solutions, suspensions, and others. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend as upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

The magnitude of a prophylactic or therapeutic dose of the pharmaceutical composition of the invention will vary with the severity of the condition to be treated and the route of administration. The dose, and perhaps the dose frequency, will also vary according to the age, body weight, and response of the individual patient.

Useful dosages of the conjugates of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one embodiment, the composition is formulated for intratumoral administration.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

The following examples are presented in order to more fully illustrate some embodiments of the invention. They should, in no way be construed, however, as limiting the scope of the invention.

Materials & Methods

All chemicals were of reagent grade and obtained from Sigma-Aldrich (Rehovot, Israel), unless otherwise mentioned. For uncaging the cCPP, filtered UV lamp (Vilber Lourmat, VL-6-L 700 μW/cm2 at 15 cm) was used on samples in a closed box covered with aluminum foil. Fmoc-protected (1-) amino acids and resins were purchased from Novabiochem. HBTU was purchased from GL biochem (Shanghai). HOBT was purchased from Luxembourg Industries. MAP was purchased from Polysciences, Inc (Warrington, Pa.). FITC was purchased from Fluka. p-Nitrophenol, tertbutyl carbazate and Levulinic acid were purchased from Acros Organics. LysoTracker was purchased from Invitrogen.

Synthesis of Peptides and Monomers

The monomers methacryloyl-glycylglycine p-nitrophenyl ester (MA-GG-ONp), methacryloyl-glycylglycine hydrazide-Boc (MA-GG-HZBoc), methacryloyl-aminopropyl fluorescein-5-isothiocyanate (MAP-FITC) and HPMA were synthesized as described previously. All peptides were synthesized on solid-phase Rink-Amide MBHA resin using the Fmoc-based chemistry. Peptide synthesis grade solvents (DMF and CH2Cl2), coupling reagent full name (HBTU) and base full name (DIPEA) were used for all syntheses. The peptides were purified by semi-preparative HPLC (Thermo-Finnegan), and their identity and purity were analyzed by analytical HPLC (Dionex), NMR (Bruker 400 MHz) and LCMS (Thermo).

KRRMKNvocWKNvocKNvoc; cCPP

The fully caged CPP was synthesized with 3 Lys side chain orthogonally protected by the 4-methyltrityl (Mtt) group. After synthesis of the fully protected peptide, the Mtt groups were selectively removed with 1% trifluoroacetic acid (TFA) in dry dichloro methane (DCM), repeating 10 times for 2 minutes each time. The free ε-amine of the Lys side chain reacted with 4,5-dimethoxy-2-nitrobenzyl formate (Nvoc-Cl) (5 mol equivalents relative to the resin loading), N-hydroxybenzotriazole (HOBT) as coupling reagent (5 eq.) and DIPEA base (10 eq.) in dry DCM containing 1M LiCl, for 3 h and then again for 12 h. The caged peptide, equipped with the photocleavable group at the desired positions, was obtained after cleavage and deprotection with the common cleavage mixture (95% TFA). MALDI-TOF. Found: 1877.58 and 939, calculated for M, and M/2 respectively.

Levulinic acid-$_D$(KLAKLAK)$_2$; KLAK. The proapoptotic peptide $_D$(KLAKLAK)$_2$ was prepared using the Fmoc method on a Rink Amide MBHA resin. The fully protected $_D$(KLAKLAK)$_2$ was then reacted with 4-oxopentanoic acid (Levulinic acid, 5 eq), HBTU (5 eq) and DIPEA (20 eq) in dry DMF for 3 h. The ketone containing peptide KLAK was obtained after cleavage and global deprotection with the common cleavage mixture (95% TFA). MALDI-TOF. Found: 1622.121 and 1645.53, calculated for M, and M+Na+ respectively.

Polymer Synthesis

The FITC-labeled HPMA copolymer precursor having active ester groups for peptide attachment (M-(GG-ONp)-FITC) and the copolymer precursor with active ester groups and protected hydrazone bonds (M-(GG-ONp)-HZBoc) were synthesized by random radical precipitation copolymerization as described previously31. The number of ONp groups in both M-(GG-ONp)-FITC and M-(GG-ONp)-HZBoc copolymer precursors was estimated by following the UV absorption (400 nm) during the release of p-nitrophenol from the copolymers in 1 N sodium hydroxide solution. FITC loading was determined from its UV absorbance at 492 nm. The amount of MA-GG-HZBoc moieties was assessed by 1H NMR in D20, using the Boe t-butyl protons chemical shift (δ 1.40, s, 9H) for the calculation. The weight average molecular weight (Mw) and polydispersity (I) of the copolymers were determined by SEC, using Sephacryl 16/60 S-400 column (GE Healthcare) with PBS buffer pH 7.4, calibrated with fractions of known molecular weight HPMA copolymers.

Synthesis of FITC Labeled-HPMA-cCPP Copolymer Conjugate, M-(cCPP)-FITC cCPP was coupled to copolymer precursors containing reactive ONp ester groups (M-(GG-ONp)-FITC) via aminolysis in dark. Briefly, the polymer precursor M-(GG-ONp)-FITC (20 mg) was dissolved in anhydrous DMSO (0.5 mL) containing TEA (80 µL) and was then reacted with the cCPP (3 mg) containing N-terminal lysine for 48 h. To remove remaining ONp ester the mixture was diluted with 2 ml of DDW pH 9 for 2 h. The reaction mixture was purified twice on PD-10 column and lyophilized. The Mw of M-(cCPP)-FITC was estimated by SEC on FPLC system using Sephacryl S-400 column. The content of conjugated peptide was estimated by H-NMR. A control polymer without cCPP (M-FITC) was obtained by releasing ONp groups from M-(GG-ONp)-FITC in 1 N sodium hydroxide solution followed by purification on PD-10 column.

Synthesis of D(KLAKLAK)2 Containing HPMA-cCPP Copolymer, M-(cCPP)-KLAK

The $_D$(KLAKLAK)$_2$ containing copolymer was prepared by a three-steps procedure. cCPP was first attached to the M-(GG-ONp)-HZBoc by aminolysis as described above, the Boe protecting groups were removed by concentrated TFA, and Lev-$_D$(KLAKLAK)$_2$ was attached to the free hydrazone groups via the ketone group of levulinic acid. For the last step, the intermediate copolymers with free hydrazone linkage, M-(cCPP)-HZ was dissolved in anhydrous methanol to a 10 wt % solution, and 60 mol % of Lev-$_D$(KLAKLAK)$_2$ (relative to the hydrazide content) was added under stirring. The reaction was performed in the dark for 48 h after adding catalytic amount of acetic acid, as described 23 and terminated by the precipitation of the polymer in diethyl ether. The conjugate was isolated and purified on LH-20 column using methanol as eluent. M-(cCPP)-KLAK conjugate was characterized by SEC on FPLC system, using Sephacryl S-400 column. The total $_D$(KLAKLAK)$_2$ content was determined by quantitative ninhydrin assay of primary amines (identifying lysine residues in the sequence).

Uncaging kinetics of cCPP. cCPP (200 µM) was dissolved in 100 µL MOPS buffer at pH=7.4 and exposed to UV light illumination (UV lamp 6 W; =365 nm). Aliquots (30 µL) were removed at various time points, immediately kept frozen, in dark until analyzed by HPLC. The molar fraction of cCPP was calculated from its HPLC peak area.

Cell Cultures and Cellular Uptake

PC-3, SW480, A431 and 3LL cells were grown in DMEM suspension culture medium supplemented with 10% fetal calf serum, 2 mM glutamine and penicillin/streptomycin (100 U/ml, 100 mg/ml) (all from Biological Industries, Kibbutz Beit-Haemek, Israel). Uptake of copolymers by various cells was estimated by flow cytometry (GUAVA Mini Easycyte) system. Cell monolayers were incubated with incubated with FITC-labeled copolymer (M-(cCPP)-FITC, 40 µg/ml) in DMEM growth medium for 2 h. Control cells were incubated in medium under the same conditions. After incubation, cells were washed twice with medium, trypsinized, collected, rinsed with cold PBS and the cell-associated fluorescence was determined immediately using flow cytometry (excitation at 485 nm, emission at 525 nm). For uncaging of M-(cCPP)-FITC the copolymer in PBS was illuminated for 10 min with UV A (365 nm, 6 W) prior to experiments.

Confocal Microscopy

Lysotracker Red DND99 (Molecular Probes, Leiden, The Netherlands) was selected to visualize lysosomes. Cells ($3\times10^4$) were seeded onto cover slips in 24-well plate with 500 DMEM growth medium. 24 h after seeding, 50 µg/ml of the FITC-labeled copolymers were added to the cells. Cells were illuminated with UV light for 8 min (365 nm, 6 W) and then incubated for 2 h. Cells were subsequently rinsed three times with medium and exposed to Lysotracker (50 nm, 60 min, 37° C.), after which they were rinsed three times with cold PBS, fixed in 3% paraformaldehyde, stained with DAPI and mounted in Mowiol-DABCO mounting medium (Aldrich Chemical Co., Milwaukee, Wis.; Sigma, St. Louis, Mo., respectively). Images were acquired with an Olympus FV1000-IX81 Confocal Microscope (excitation at 488 nm, emission collected with a 515 nm barrier filter), followed by a red filter analysis (excitation at 543 nm, emission collected with a 570 nm barrier filter). Auto-fluorescence background was ascertained using control (untreated) cells.

Caging Via Reversible Electrostatic Interactions

HPMA-CPP-FITC conjugate was mixed with various polyanions such as Polyglutamic acid (PGA); Fucoidan (FI); Heparin sulfate (Hep) Hyaluronic acid (HA); Low molecular weight heparin (LMWH), Amberlite IR120 (Amb) or Polyglycylglycine (P-GG) at a weight ratio of 3:1 or 5:1 in PBS. The solutions were left for 10 min at room temperature to allow HPMA-CPP-FITC-polyanion complex formation, and then added to B16 cell monolayers in growth medium The reversibility of masking the CPP activity in complexes was assessed following the addition of the counter polycation, protamine to the incubation medium. B16 cells were treated with HPMA-CPP-FITC-polyanion complexes for 10 min, and then the counter polycation protamine (4.7 KDa, 10-50 µg/ml, at the same weight ratio of HPMA conjugate) was added to the cells. Control cells were treated with HPMA-CPP-FITC-polyanion complexes without protamin. After 1 h, the cells were washed with PBS, harvested with trypsin and the cell associated fluorescence was analyzed by flow cytometry.

Caging is Via a Time-Released Protecting Group

HPMA-CPP-FITC conjugate was mixed with 1,2-cyclohexanedione (CHD) or 2,3-butadione (BD) (1:5 molar excess) for 2 h. The complexes were purified on Sephadex G-25 (PD10) column and lyophilized. 50 µg/ml of polymer complex was added to B16 cancer cell monolayes in growth medium. Cells were washed with PBS, harvested at different time points with trypsin and the cell related fluorescence was analyzed by flow cytometry.

Dose-Dependent Cytotoxicity Assay

The cytotoxicity of M-cCPP-KLAK, M-cCPP and o(KIAKLAK) (SEQ ID NO: 5)2, was assessed using a modified 3-(4,5-dimethylthiazol-2-yl)-2,5-diphenyltetrazolinium bromide (MTT). All concentrations of KLAK-HPMA copolymers used for these experiments are expressed in KLAK equivalents. All solutions were sterilized by filtering through a 0.2-µm membrane filter. Cells were seeded into 96-well microtitre plates at a density of 80,000 cells per well. Twenty-four hours after seeding, the sterile compounds M-cCPP-KLAK, M-cCPP) and ($_D$(KLAKLAK (SEQ ID NO: 5))$_2$, in fresh media were added and cells were exposed to UV light illumination for different time intervals or kept in the dark. Cells were then further incubated in the dark for 2.5 h. Cell survival assay was performed by discarding the medium followed by the addition of 100 µl of fresh medium and 25 µl of 5 mg/ml MTT solution in DPBS to each well and incubating for 3 hours. The medium was discarded and 100 µl of DMSO were added to dissolve Formazan crystals. The absorbance of each sample was measured at 570 nm.

Example 1

Synthesis of Targetable Polymer-CPP Conjugates

Figure 2:
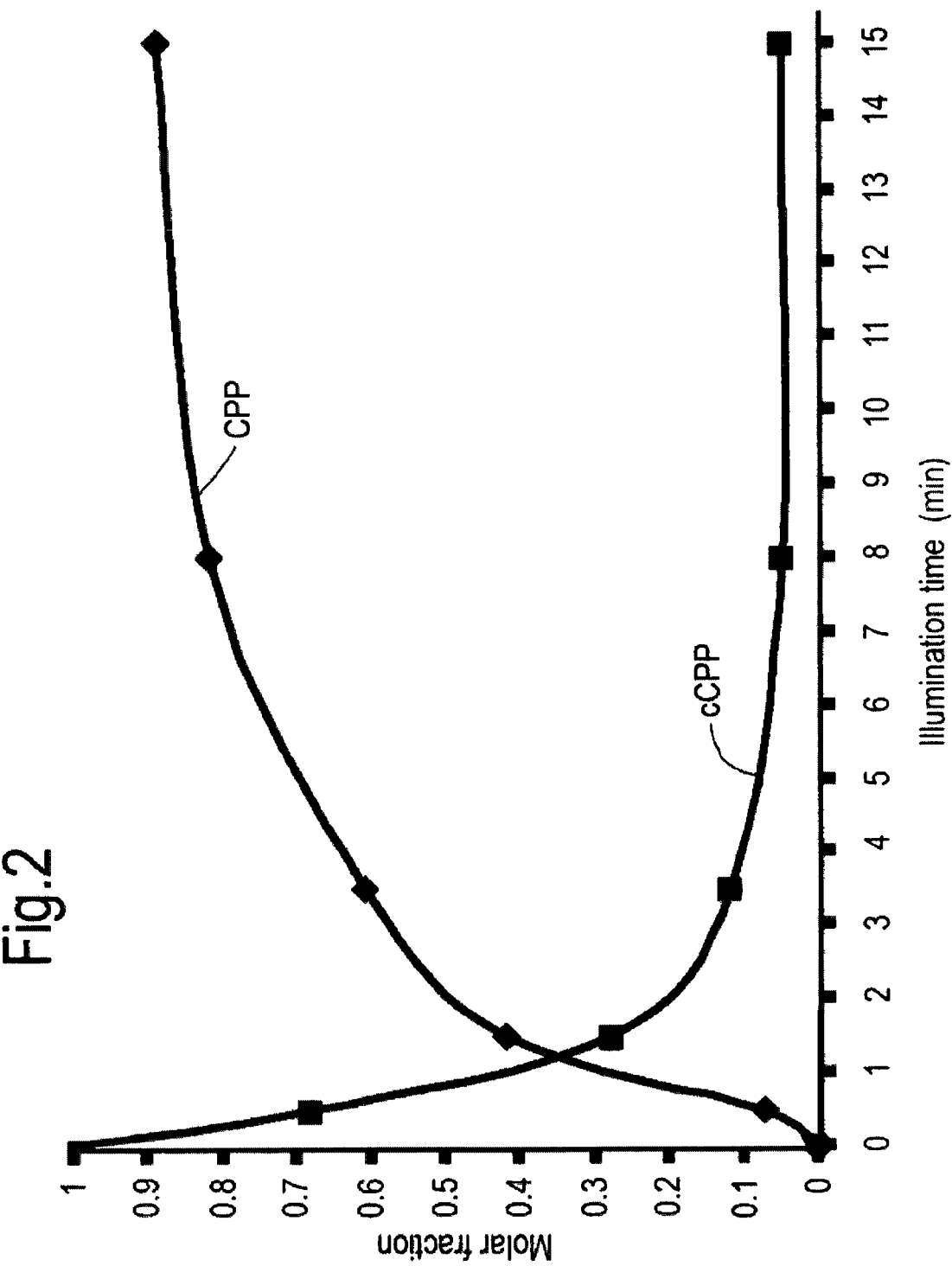
FIG. 2 depicts the uncaging kinetics of cCPP as a function of light illumination time (365 nm) as determined with HPLC.

CPP with 3 Mtt-protected Lys, Ac-KRRMK$^{Mtt}$WK$^{Mtt}$K$^{Mtt}$ (KRRMKWKXK SEQ ID NO: 6) was synthesized on a solid phase via Fmoc chemistry on a MBHA Resin. CPP was then modified to include 3 photolabile protecting groups on Lys side chains to give the caged CPP (cCPP), Ac-KRRMK$^{Nvoc}$WK$^{Nvoc}$K$^{Nvoc}$. The identity and purity (>90%) were determined by HPLC and MALDI-TOF mass spectrometer. In order to study the uncaging kinetics of the peptide, a solution of cCPP (200 μM) was exposed to UV light illumination (700 μW/cm2; λ=365 nm). Aliquots were removed at various time points, and then evaluated by high performance liquid chromatography with UV detection (HPLC-UV) at 230 nm. The molar fraction of cCPP was calculated from its HPLC peak (FIG. 2). 8 minutes of illumination were sufficient to attain >80% of uncaged CPP, and thus further experiments were therefore undertaken with 8-10 min of light illumination. The low illumination intensity (700 μW/cm$^2$ 0.5 J/cm$^2$) at λ$_{365\ nm}$ is known to be relatively non toxic to cells.

The amine terminated cCPP was conjugated to FITC labeled HPMA copolymer precursor having active p-nitrophenyl ester groups (ONp) (designated as M-(GG-ONp)-FITC, where M represents the HPMA copolymer backbone) or to copolymer precursor with ONp groups and protected hydrazone bonds (M-(GG-ONp)-HZBoc), which later used for KLAK attachment. M-(GG-ONp)-FITC and M-(GG-ONp)-HZBoc were first synthesized by random radical precipitation copolymerization of HPMA, MA-GG-ONp and MAP-FITC or MA-GG-HZBoc, as described previously (Shamay et al., Biomaterials, 2009, 30, 6460-8). The estimated weighted average molecular weight (Mw) of M-(GG-ONp)-FITC was 23 kDa, and the copolymer contained 1.8 mol % of MAP-FITC and 8 mol % of MA-GG-ONp (Table 1).

TABLE 1

Characteristics of FITC labeled HPMA-cCPP copolymer conjugates

| HPMA Conjugate | MW | I | % mol FITC | % mol ONP or COOH | % mol cCPP | Number of peptide per macromolecule |
|---|---|---|---|---|---|---|
| M-(GG-ONP)-FITC$^a$ | 23000 | 1.42 | 1.8 | 8.3 | 0 | 0 |
| M-cCPP-FITC | 23000 | 1.42 | 1.8 | 7.3 | 1 | 2 |
| M-FITC | 23000 | 1.42 | 1.8 | 8.3 | 0 | 0 |

M-(GG-ONp)-HZBoc contained 7.7 mol % and 6.4 mol % of MA-GG-ONp and MA-GG-HZBoc, respectively (Table 2).

TABLE 2

Characteristics of KLAK containing HPMA-cCPP copolymer conjugates

| HPMA Cojugate | MW | I | % Mole KLAK | % mol HZBOC | % mol ONP | % mol cCPP | Number of KLAK per macromolecule |
|---|---|---|---|---|---|---|---|
| M-(GG-ONP)-HZBOC | 19600 | 1.37 | 0 | 6.4 | 7.7 | 0 | 0 |
| M-cCPP | 19600 | 1.37 | 0 | 6.4 | 0 | 1 | 0 |
| M-cCPP-KLAK | 19600 | 1.37 | 5 | 1.4 | 0 | 1 | 6 |

Figure 3A:
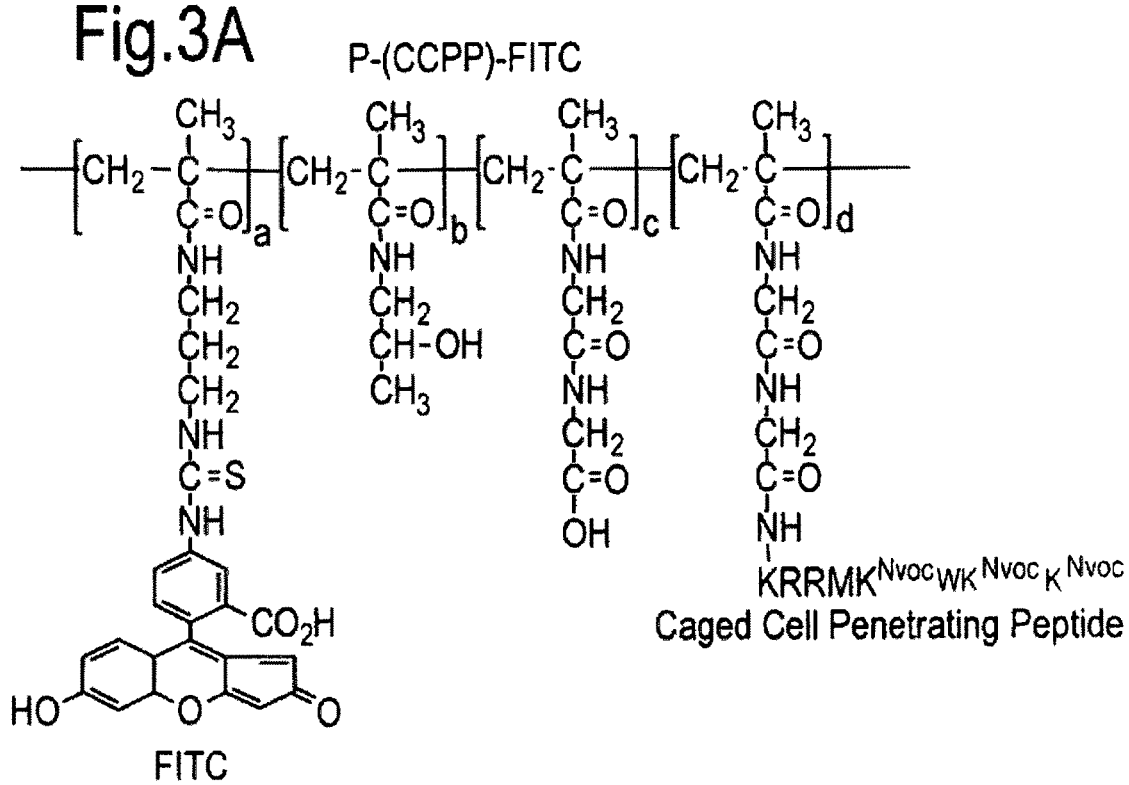
FIG. 3A and FIG. 3B depict the structure of light activated HPMA copolymers bearing cCPP.
Figure 3B:
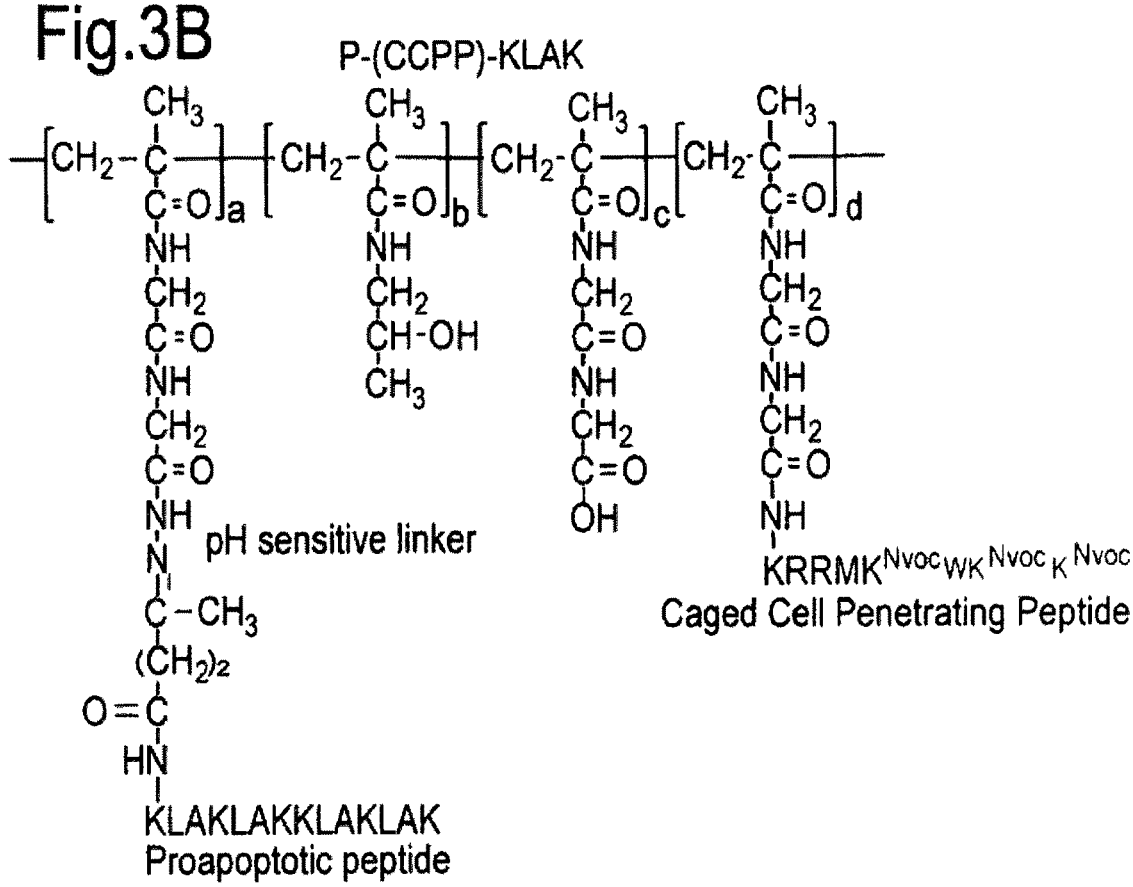
Figure 4A:
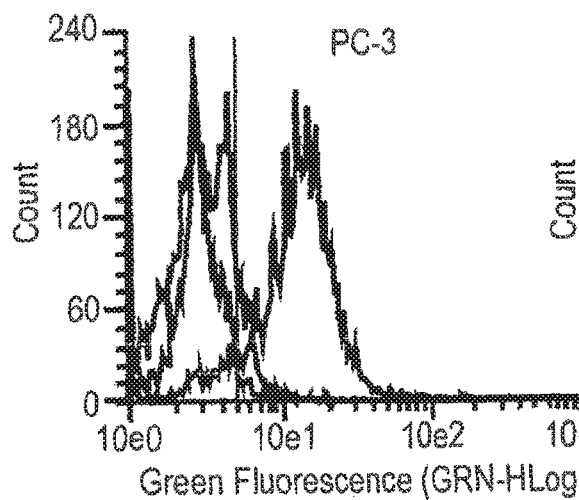
FIG. 4A-FIG. 4D depict light activated cell penetration of M-(cCPP)-FITC in various cell lines. Cells were incubated with 40 μg/ml M-(cCPP)-FITC or M-FITC (control) and illuminated with of UV Light (700 μW/cm2; λ=365 nm) for 10 minutes or kept in the dark, followed by 2 h incubation at 37° C. The cell associated fluorescence was measured by flow cytometry (excitation at 492 nm, emission at 525 nm).
Figure 4B:
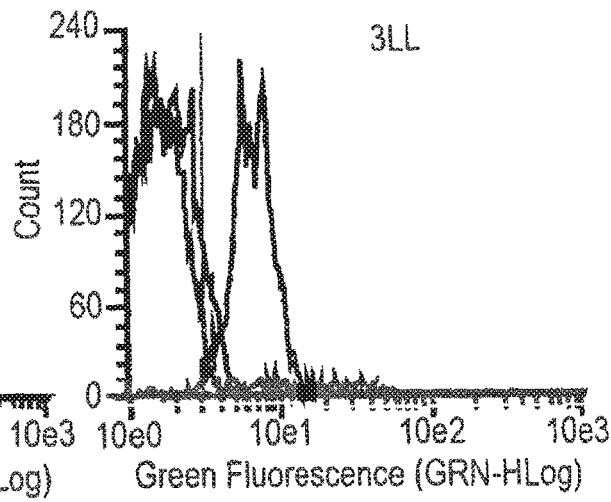
Figure 4C:
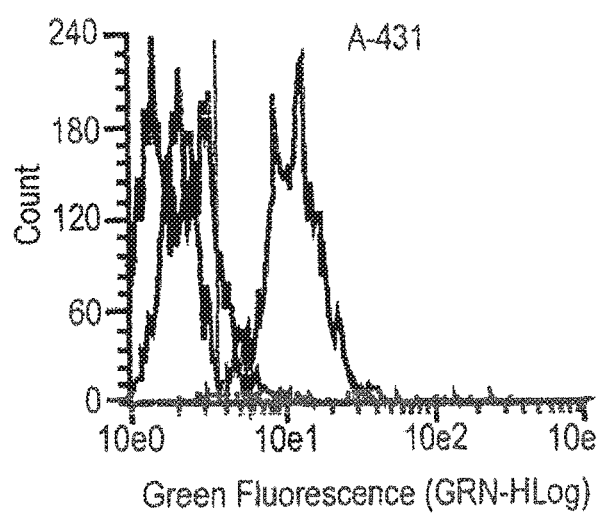
Figure 4D:
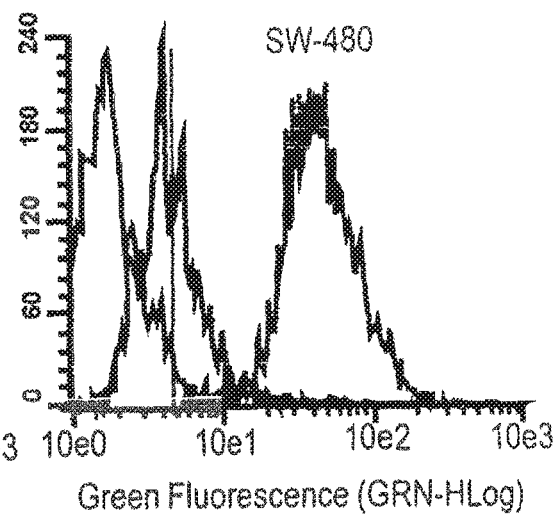
Figure 5C:
FIG. 5A-FIG. 5F depict light activated penetration of M-(cCPP)-FITC into PC-3 cells in situ. Cells were incubated with 50 μg/ml M-(cCPP)-FITC and illuminated with of UV Light (700 μW/cm2; λ=365 nm) for 10 minutes or kept in the dark, followed by 2 h incubation at 37° C. At the end of the first hour LysoTracker Red DND-99 was added to the medium to visualize lysosomes. Cell-fluorescence was imaged by fluorescence confocal microscopy.
Figure 5F:
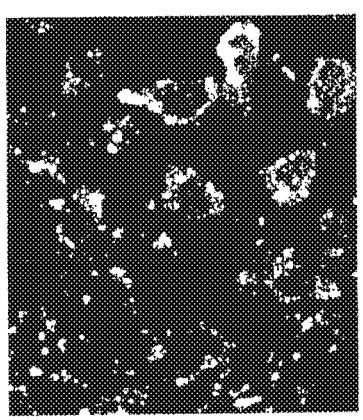
Figure 5B:
Figure 5E:
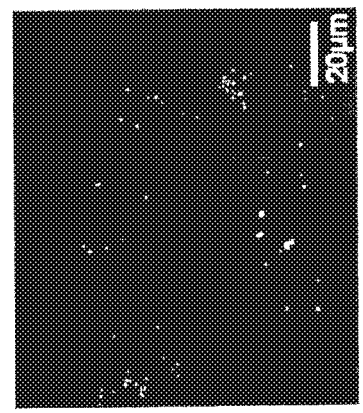
Figure 5A:
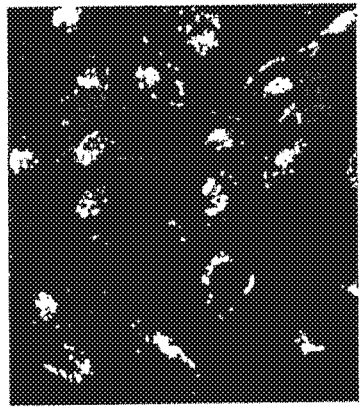
Figure 5D:
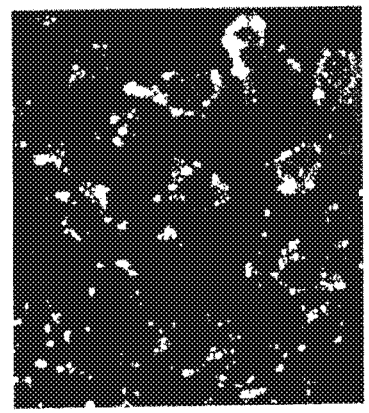
Figure 9A:
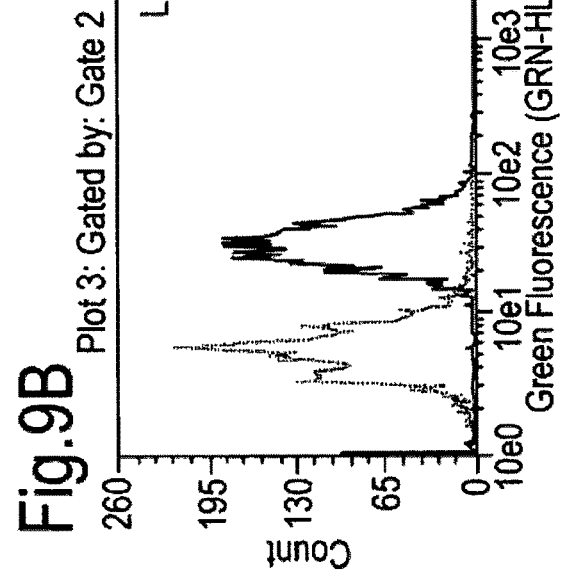
FIG. 9A-FIG. 9D depict the reversible masking of CPP activity by polyanion complexes via the addition of protamine.
Figure 9B:
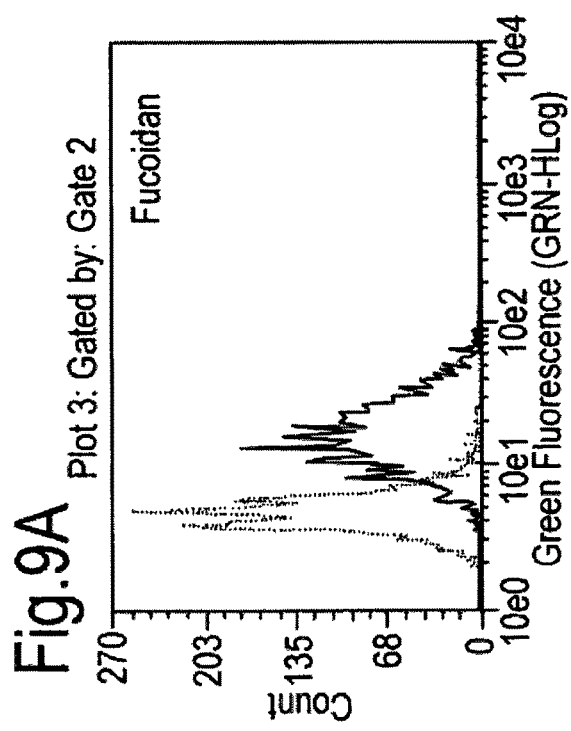
Figure 9D:
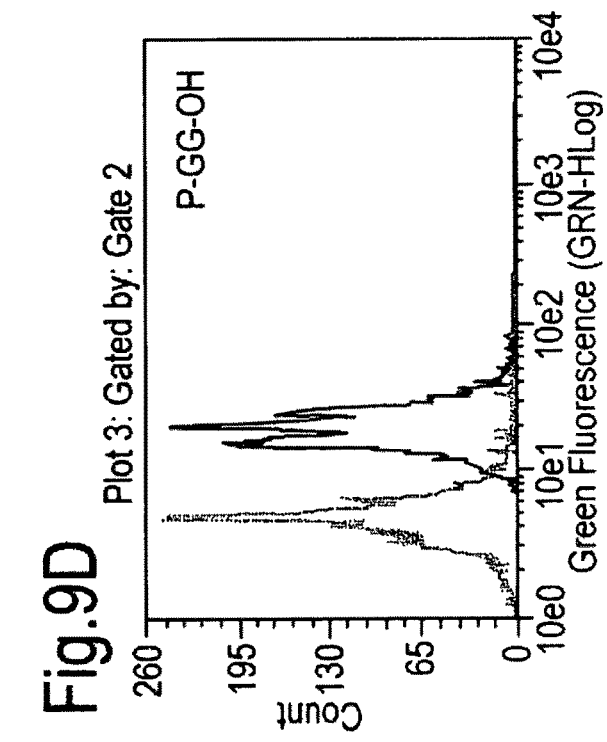
Figure 9C:
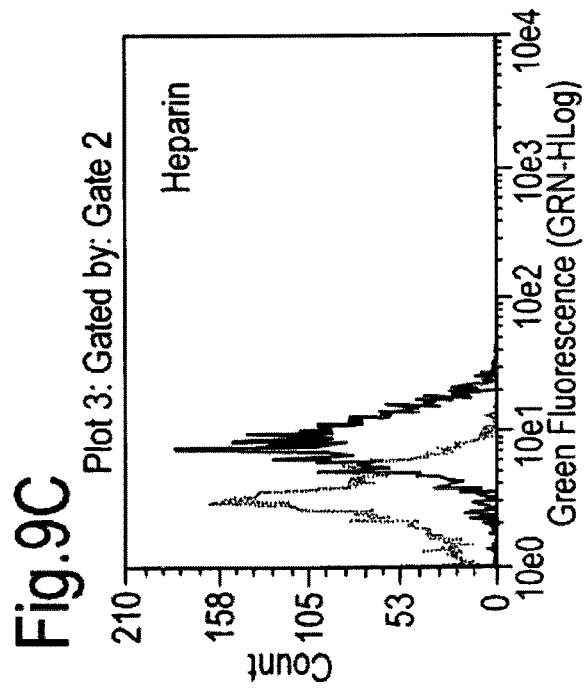

The ε-amino group of the N-terminal lysine of cCPP was then coupled to M-(GG-ONp)-FITC and M-(GG-ONp)-HZBoc by aminolysis, while keeping the other three ε-amines protected with the photolabile group Nvoc (FIG. 3A and FIG. 3B). Since cCPP still contains 2 positively charged arginine residues in its sequence, the total amount of cCPP in the polymer was limited to 1 mol %. This low mol % of cCPP ensures that the net charge of the caged polymer will be negative owing to the excess (7 mol %) carboxylic acids of un-conjugated linker (Gly-Gly-COOH). M-(cCPP)-KLAK copolymer was prepared by removal of the Boc protecting groups from the hydrazone groups, and subsequent reactions with the carbonyl group of Levulinic acid (Lev)-containing $_D$(KLAKLAK)$_2$ (KLAK) with the free hydrazone end groups. The pH sensitive hydrazone bond on the copolymer backbone is relatively stable in the blood circulation at pH 7.4, but hydrolytically degradable in mildly acidic environment (pH 5-6), thus can facilitate drug release at endosomal or lysosomal compartments of the target cells. The Mw, polydispersity (I), and mol percent side chain loading of FITC, HZBoc and peptides, as obtained for the precursor copolymer are shown in Tables 1 and 2.

Example 2

Targetable Polymer-CPP Conjugates are Internalized within Cells

To demonstrate that polymers with cCPP can penetrate cells only upon light activation, various cell line monolayers (prostate cancer (PC-3); human epithelial carcinoma (A431); colon-adenocarcinoma (SW480); and Lewis lung carcinoma (3LL)) were incubated with 40 μg/ml M-(cCPP)-FITC or M-FITC (without cCPP as control) in growth medium and exposed to 10 min of UV-light illumination (k=365 nm, 700 μW/cm2) followed by 2 h incubation in 37° C. Cells were then washed twice with medium, trypsinized, collected and the cell-associated fluorescence was determined immediately using flow cytometry (GUAVA MiniEasycyte system) (FIGS. 4A-4D). The results after 2 h (FIGS. 4A-4D) clearly confirm the removal of the caging group by light stimuli for regaining CPP activity in all tested cells. Cell labeling increased by 20-100-fold when illuminated. Similar fluorescence intensity was measured in illuminated cells incubated with M-F1TC or in non-illuminated cells treated with M-(cCPP)-FITC. This shows that light illumination generates a switch-like behavior with 100% of fluorescently-labeled cells. Since trypsin treatment removes most of membrane-bound polymers, the measured fluorescence is related to internalized conjugate.

Confocal microscopy was used to evaluate the sub-cellular fate of the F1TC-labeled copolymers following light illumination in PC-3 cells in situ. Cells were incubated with the M-(cCPP}-FITC and either illuminated (λ=365 nm, 700 μW/cm2) for 8 min or kept in dark followed by 2 hours incubation in growth medium at 37° C. FIGS. 5A-5F confirms the rapid internalization of the polymer with cCPP upon light illumination, and to a significantly lower extent by non-illuminated cells. The colocalization of the lysosomal marker (Lysotracker Red) and M-(cCPP)-FITC on the illuminated cells, indicated that the copolymer was taken up by the cells and transported into lysosomal compartments, which are suitable for release of drugs through pH sensitive linkers like the hydrazone bond. Fluorescence was also detected at the plasma membrane and in the cytoplasm after illumination. In contrast, no fluorescence was noted in non-illuminated cells incubated with M-(cCPP)-FITC after 2 hours of incubation. This validates the flow cytometry data which indicates that cCPP remains inactive and restores its activity only after light illumination.

Example 3

In Vivo Application of Targeted Copolymers

In order to demonstrate the ability of polymer with cCPP to provide control over cell cytotoxic activity, the light-mediated cytotoxicity of M-{cCPP}-KLAK was studied by following its growth-inhibitory activity against PC-3 cells over time (FIGS. 6A and 6B). Twenty-four hours after seeding, cells were incubated with M-(cCPP)-KLAK, M-(cCPP) (control vehicle) and KLAK, (free drug) and illuminated for different time periods. Cell viability was tested 2.5 hours after illumination by MTT assay. FIG. 6A demonstrates that cytotoxicity of M-{cCPP}-KLAK was dependent on the drug concentration and duration of light illumination. 3.5 minutes of light illumination were sufficient to kill 50% of treated cells ($IC_{50}$) with M-{cCPP}-KLAK at 80 µM KLAK equivalent. The $IC_{50}$ dose of M-(cCPP)-KLAK at 40 µM and 20 µM KLAK was attained only after 6 and 8 minutes of illumination, respectively. The KLAK peptide is known to disrupt the negatively charged mitochondrial membrane only when internalized, and its toxicity can be observed almost instantly. Since free KLAK peptide cannot penetrate the cell membrane26 no significant toxicity was demonstrated towards PC-3 cells at 80 µM dose even after 15 min of light illumination. The polymer without drug M-(cCPP) had no toxic effects against PC-3 cells at the highest (80 µM) equivalent dose of M-(cCPP)-KLAK even after 15 minutes of light illumination. This indicates that the caging molecule Nvoc had no effect on cell viability after cleaved. Cell cytotoxicity was further tested in A431, 3LL, SW480 and PC-3 cells at the same (60 µM KLAK equiv) dose following 8 min light illumination (FIG. 6B). Cells were incubated with M-(cCPP)-KLAK, M-(cCPP) and KLAK and exposed to light illumination or kept in dark followed by 2.5 h incubation. The cell viability, as measured by the MIT assay, demonstrated a 'light switch' cytotoxicity for M-(cCPP)-KLAK, with 90-100% viable cells kept under dark and a significant toxicity (only to 10-20% viable cells) upon illumination. These findings clearly indicate that light illumination enhances the penetration of the polymer-CPP conjugates into target cells and promote more effective intracellular delivery of the pro-apoptotic anticancer model drug.

Example 4

Regulated Systems for Reversible Caging of Targeted Copolymers

In order to demonstrate the versatility of the platform for the polymer-CPP conjugates additional regulated systems for reversible caging mechanisms were developed. Caging via reversible electrostatic interactions and caging via time-released protecting groups were prepared and evaluated.

HPMA-CPP-FITC conjugate was mixed with different polyanions (Hep, Fl, PGA, HA, P-GG, LMWH, Amb) and then added to B16-cell monolayers and compared to control cells treated with HPMA-CPP-FITC conjugate alone (FIGS. 7A-7D). The mean fluorescence intensity was significantly reduced following pre-treatment with Hep, LMWH, Fl, PGA, PGG 100%, and Amb, due to the efficient masking of the CPP activity. HPMA-CPP-FITC polyanion complexes incubated with B-16 cells over time demonstrated a reduced fluorescence intensity which was stable for at least 6 hours (FIGS. 8A-8D).

The masking of CPP activity by the polyanion complexes was readily reversible following the addition of the polycation, protamine (4.7 KD) (FIGS. 9A-9D). Greater intensity is readily seen in protamine treated (black lines) versus untreated (gray lines) samples.

The efficiency of polyanion release from HPMA-CPP-FITC complexes by protamine was at the following order: LMWH>P-GG100%>Fl>Hep (corresponding to outermost versus innermost graphs) (FIG. 10).

Figure 11:
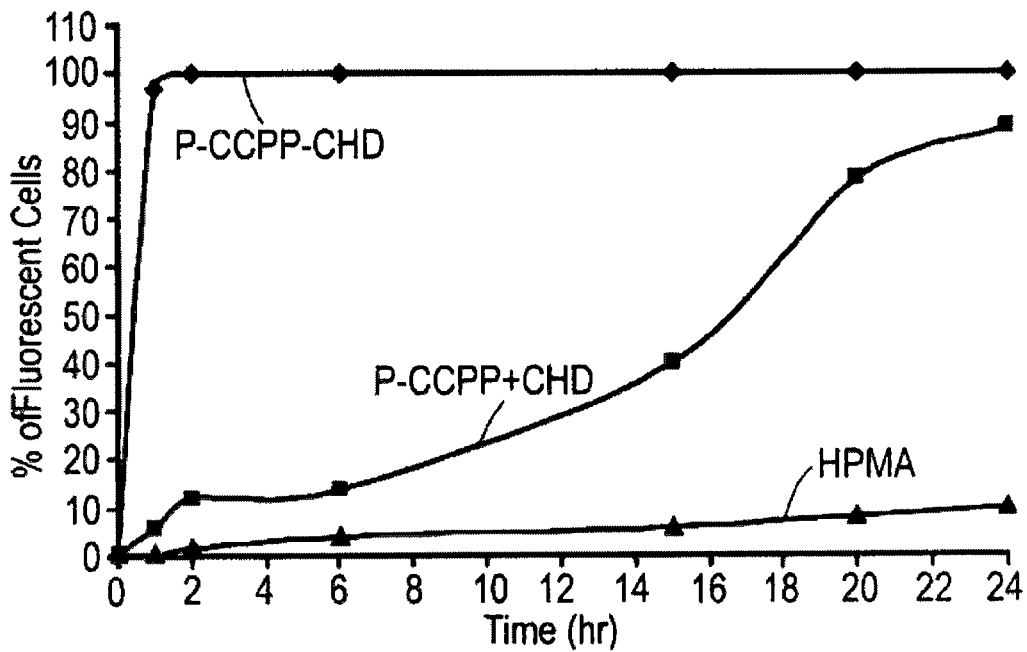
FIG. 11 depicts a time control caged peptide system using 1,2-cyclohexanedione. Formed HPMA-CPP-FITC (P-CPP)-CHD complexes were added to B16 cell monolayers. After 15 h, 40% of the CPP activity was regained. 100% of CPP activity was attained by 24 h post treatment.

Reversible caging via a time-release mechanism is accomplished via the use of protecting groups, as well. An HPMA-CPP-FITC (P-CPP)-CHD complex was formed and then added to B16 cell monolayers. After 15 h, 40% of the CPP activity was regained. 100% of CPP activity was attained 24 h post treatment (FIG. 11) showing the reversible caging over time in this system.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method of imaging a cancerous cell or cancerous tissue or an inflamed tissue in a subject in need thereof, the method comprising:

a) contacting the cancerous cell or cancerous tissue or contacting the inflamed tissue with a caged cell penetrating peptide (cCPP)-macromolecular carrier conjugate of formula 1:

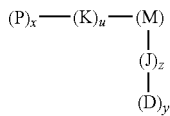

wherein x, y, u, and z are independently percentages of the respective element composition of the conjugate, wherein x is present from 0.05%-50%, y is present from 0-50%, u is present from 0-50% and z is present from 0-50%;

P is a caged cell penetrating peptide, wherein the amino acid sequence of the cell penetrating peptide comprises the amino acid sequence KRRMKWKK;

M is a macromolecular carrier molecule consisting of underivatized monomers selected from the group consisting of N-(2-hydroxypropyl)methacrylamide (HPMA), N-methylacrylamide, N,N-dialkylacrylamides, acrylic acid, polyethylene glycol, methacrylic acid, polyamino acids, polysaccharides, polyvinyl pyrrolidone-maleic anhydride polymers, polylactic-co-glycolic acid, and combinations thereof;

D is a detectable agent or a therapeutic agent, or a combination thereof, wherein the detectable agent is fluorescent, radioactive, luminescent or electron dense, and wherein the therapeutic agent is a toxin, a chemotherapeutic agent, $_D$(KLAKLAK)$_2$, KLAK, a radioisotope, an antimetabolite, a microtubule inhibitor, or a combination thereof; and J and K are spacer molecules;

b) uncaging the cCPP, wherein the conjugate is specifically internalized within the cancerous cell or cancerous tissue or inflamed tissue, or cells proximally located thereto; and c) imaging the cancerous cell and cancerous tissue or the inflamed tissue of the subject by detecting the uptake of the detectable agent D of the conjugate by the cancerous cell or cancerous tissue or by the inflamed tissue.

2. The method of claim 1, wherein the method further comprises:

d) diagnosing the presence of a cancerous cell or cancerous tissue in the subject, by detecting uptake of the detectable agent D of the conjugate by the cancerous cell or cancerous tissue in step (c); and e) selecting the subject in (d) for an anti-cancer treatment or therapy.

3. The method of claim 1, wherein the uncaging occurs as a function of time.

4. The method of claim 1, wherein the uncaging occurs following exposure of a region comprising the conjugate to a light source.

5. The method of claim 1, wherein the uncaging occurs following exposure to protamine.

6. The method of claim 2, wherein the method further comprises providing an anti-cancer therapy to the subject.

7. The method of claim 6, wherein the anti-cancer therapy comprises surgery, chemotherapy, radiation or a combination thereof.

8. The method of claim 2, wherein the detection is an optical detection.

9. A method of treating a cancerous cell or cancerous tissue or an inflamed tissue in a subject in need thereof, the method comprising:

a) contacting a cancerous tissue or cancerous tissue or the inflamed tissue of the subject in need thereof with an effective amount of a caged cell penetrating peptide (cCPP)-macromolecular carrier conjugate of formula 1:

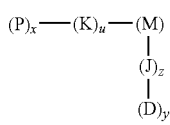

wherein x, y, u, and z are independently percentages of the respective element composition of the conjugate, wherein x is present from 0.05%-50%, y is present from 0-50%, u is present from 0-50% and z is present from 0-50%;

P is a caged cell penetrating peptide, wherein the amino acid sequence of the cell penetrating peptide comprises the amino acid sequence KRRMKWKK;

M is a macromolecular carrier molecule consisting of underivatized monomers selected from the group consisting of N-(2-hydroxypropyl)methacrylamide (HPMA), N-methylacrylamide, N,N-dialkylacrylamides, acrylic acid, polyethylene glycol, methacrylic acid, polyamino acids, polysaccharides, polyvinyl pyrrolidone-maleic anhydride polymers, polylactic-co-glycolic acid, and combinations thereof;

D is a detectable agent or a therapeutic agent, or a combination thereof, wherein the detectable agent is fluorescent, radioactive, luminescent or electron dense, and wherein the therapeutic agent is a toxin, a chemotherapeutic agent, $_D$(KLAKLAK)$_2$, KLAK, a radioisotope, an antimetabolite, a microtubule inhibitor, or a combination thereof; and J and K are spacer molecules;

b) uncaging the cCPP, wherein the conjugate is specifically internalized within the cancerous cell or cancerous tissue or inflamed tissue, or cells proximally located thereto; and c) delivering the therapeutic agent of step (a) inside the cancerous cell or cancerous tissue or inside the inflamed tissue of the subject in need thereof.

10. The method of claim 9, wherein the therapeutic agent ameliorates or abrogates cancer pathogenesis in the subject.

11. The method of claim 2, wherein the anti-cancer therapy is selected from the group consisting of surgery, chemotherapy, radiation or a combination thereof.

* * * * *